US012102341B2

(12) United States Patent
Ogle

(10) Patent No.: US 12,102,341 B2
(45) Date of Patent: *Oct. 1, 2024

(54) SUCTION CATHETER SYSTEMS FOR APPLYING EFFECTIVE ASPIRATION IN REMOTE VESSELS, ESPECIALLY CEREBRAL ARTERIES

(71) Applicant: MIVI Neuroscience, Inc., Eden Prairie, MN (US)

(72) Inventor: Matthew F. Ogle, Edina, MN (US)

(73) Assignee: MIVI Neuroscience, Inc., Eden Prairie, MN (US)

( * ) Notice: Subject to any disclaimer, the term of this patent is extended or adjusted under 35 U.S.C. 154(b) by 343 days.

This patent is subject to a terminal disclaimer.

(21) Appl. No.: 17/549,351

(22) Filed: Dec. 13, 2021

(65) Prior Publication Data
US 2022/0096104 A1 Mar. 31, 2022

Related U.S. Application Data

(63) Continuation of application No. 15/848,166, filed on Dec. 20, 2017, now Pat. No. 11,234,723.

(51) Int. Cl.
*A61B 17/22* (2006.01)
*A61M 1/00* (2006.01)
(Continued)

(52) U.S. Cl.
CPC ............... *A61B 17/22* (2013.01); *A61M 1/00* (2013.01); *A61M 1/71* (2021.05); *A61M 1/732* (2021.05);
(Continued)

(58) Field of Classification Search
CPC ...... A61M 1/71; A61M 1/84; A61M 25/0068; A61M 25/0074; A61M 27/006;
(Continued)

(56) References Cited

U.S. PATENT DOCUMENTS 2,730,101 A 1/1956 Hoffman
3,565,076 A * 2/1971 Kadan .................. A61M 1/742
604/67
(Continued)

FOREIGN PATENT DOCUMENTS

CN 204158457 U 2/2015
CN 104758029 A 7/2015
(Continued)

OTHER PUBLICATIONS

Feldman, "Transcatheter Aspiration of a Thrombus in an Aortocoronary Saphenous Vein Graft," American Journal of Cardiology, 60(4):379-380 ( 1987).
(Continued)

*Primary Examiner* — Adam Marcetich
(74) *Attorney, Agent, or Firm* — Christensen, Fonder, Dardi PLLC; Andrew H. Auderieth; Peter S. Dardi

(57) ABSTRACT

A suction catheter system is described with a suction extension interfaced with a guide catheter to form a continuous suction lumen extending through a portion of the guide catheter and through the suction extension. The suction extension can be positioned by tracking the suction nozzle through a vessel while moving a proximal portion of the suction extension within the lumen of the guide catheter. The suction extension can comprise a connecting section with a non-circular cross section for interfacing with the inner lumen of an engagement section of the guide catheter. The tubular body of the guide catheter can have a reduced diameter distal section the can be useful to restrain the movement of the suction extension. Proximal fittings attached to the guide catheter can facilitate safe removal of the catheter system from the patient by allowing for the removal of some or all of a tubular extension of the suction extension from the guide catheter behind a hemostatic seal. Pressure sensors connected to the proximal fittings can help (Continued)

to guide the procedures with reduced risk of embolizing thrombus.

18 Claims, 13 Drawing Sheets

(51) Int. Cl.
    *A61M 25/00*     (2006.01)
    *A61M 25/09*     (2006.01)
    *A61M 25/10*     (2013.01)
    *A61M 27/00*     (2006.01)
    *A61B 17/00*     (2006.01)
    *A61B 17/221*     (2006.01)
    *A61B 17/3207*     (2006.01)
    *A61B 90/00*     (2016.01)

(52) U.S. Cl.
    CPC .......... *A61M 1/84* (2021.05); *A61M 25/0068* (2013.01); *A61M 25/0074* (2013.01); *A61M 27/006* (2013.01); *A61B 17/00234* (2013.01); *A61B 2017/00331* (2013.01); *A61B 2017/22079* (2013.01); *A61B 17/221* (2013.01); *A61B 2017/2212* (2013.01); *A61B 2017/320716* (2013.01); *A61B 2090/064* (2016.02); *A61B 2217/005* (2013.01); *A61M 1/74* (2021.05); *A61M 1/85* (2021.05); *A61M 25/09* (2013.01); *A61M 25/10* (2013.01); *A61M 2205/3344* (2013.01); *A61M 2210/0693* (2013.01)

(58) Field of Classification Search
    CPC .................... A61M 1/85; A61M 39/10; A61B 2017/22079; A61B 2217/005; A61B 2017/22067; A61B 2017/22084; A61B 17/12109; A61B 2217/007; A61B 2017/22001; A61B 2017/22038
    See application file for complete search history.

(56) References Cited

U.S. PATENT DOCUMENTS

| | | |
|---|---|---|
| 3,949,757 A | 4/1976 | Sabel |
| 3,996,938 A | 12/1976 | Clark, III |
| 4,020,829 A | 5/1977 | Wilson et al. |
| 4,033,331 A | 7/1977 | Guss et al. |
| 4,174,715 A | 11/1979 | Hasson |
| 4,610,662 A | 9/1986 | Weikl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engleson |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,863,431 A | 9/1989 | Vaillancourt |
| 4,873,978 A | 10/1989 | Ginsburg |
| 4,873,979 A | 10/1989 | Ginsburg |
| 4,883,460 A | 11/1989 | Zanetti |
| 4,887,613 A | 12/1989 | Farr et al. |
| 4,900,303 A | 2/1990 | Lemelson |
| 4,921,484 A | 5/1990 | Hillstead |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,161,534 A | 11/1992 | Berthaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,211,651 A | 5/1993 | Reger et al. |
| 5,219,332 A | 6/1993 | Nelson et al. |
| 5,308,318 A | 5/1994 | Plassche, Jr. |
| 5,312,338 A | 5/1994 | Nelson et al. |
| 5,325,868 A | 7/1994 | Kimmelstiel |
| 5,334,160 A | 8/1994 | Ellis |
| 5,352,197 A | 10/1994 | Hammersmark et al. |
| 5,364,358 A | 11/1994 | Hewitt et al. |
| 5,392,778 A | 2/1995 | Horzewski |
| 5,395,383 A | 3/1995 | Adams et al. |
| 5,413,575 A | 5/1995 | Haenggi |
| 5,423,331 A | 6/1995 | Wysham |
| 5,438,993 A | 8/1995 | Lynch et al. |
| 5,465,716 A | 11/1995 | Avitall |
| 5,485,667 A | 1/1996 | Kleshinski |
| 5,490,859 A | 2/1996 | Mische et al. |
| 5,501,694 A | 3/1996 | Resseman et al. |
| 5,527,292 A | 6/1996 | Adams et al. |
| 5,533,967 A | 7/1996 | Imran |
| 5,546,958 A | 8/1996 | Throud et al. |
| 5,549,626 A | 8/1996 | Miller et al. |
| 5,571,122 A | 11/1996 | Kelly et al. |
| 5,578,009 A | 11/1996 | Kraus et al. |
| 5,599,307 A | 2/1997 | Bacher et al. |
| 5,720,764 A | 2/1998 | Naderlinger |
| 5,766,191 A | 6/1998 | Treotola |
| 5,776,142 A | 7/1998 | Gunderson |
| 5,810,874 A | 9/1998 | Lefebvre |
| 5,814,064 A | 9/1998 | Daniel et al. |
| 5,817,101 A | 10/1998 | Fiedler |
| 5,836,868 A | 11/1998 | Resseman et al. |
| 5,843,002 A | 12/1998 | Pecor et al. |
| 5,843,051 A | 12/1998 | Adams et al. |
| 5,851,189 A | 12/1998 | Forber |
| 5,882,329 A | 3/1999 | Patterson et al. |
| 5,897,567 A | 4/1999 | Resseman et al. |
| 5,899,890 A | 5/1999 | Chiang et al. |
| 5,910,154 A | 6/1999 | Tsugita et al. |
| 5,911,725 A | 6/1999 | Boury |
| 5,911,734 A | 6/1999 | Tsugita et al. |
| 5,928,260 A | 7/1999 | Chin et al. |
| 5,935,139 A | 8/1999 | Bates |
| 5,938,645 A | 8/1999 | Gordon |
| 5,941,869 A | 8/1999 | Patterson et al. |
| 5,972,019 A | 10/1999 | Engleson et al. |
| 5,997,557 A | 12/1999 | Barbut et al. |
| 6,010,522 A | 1/2000 | Barbut et al. |
| 6,022,336 A | 2/2000 | Zando-Azizi et al. |
| 6,030,349 A | 2/2000 | Wilson et al. |
| 6,030,369 A | 2/2000 | Engelson et al. |
| 6,066,149 A | 5/2000 | Samson et al. |
| 6,106,530 A | 8/2000 | Harada |
| 6,117,141 A | 9/2000 | Ouchi |
| 6,135,991 A | 10/2000 | Muni et al. |
| 6,142,987 A | 11/2000 | Tsugita |
| 6,146,396 A | 11/2000 | Konya et al. |
| 6,156,005 A | 12/2000 | Theron |
| 6,159,195 A | 12/2000 | Ha et al. |
| 6,159,230 A | 12/2000 | Samuels |
| 6,168,579 B1 | 1/2001 | Tsugita |
| 6,203,561 B1 | 3/2001 | Ramee et al. |
| 6,206,868 B1 | 3/2001 | Parodi |
| 6,221,049 B1 | 4/2001 | Selmon et al. |
| 6,238,402 B1 | 5/2001 | Sullivan, III et al. |
| 6,238,412 B1 | 5/2001 | Dubrul et al. |
| 6,240,231 B1 | 5/2001 | Ferrera et al. |
| 6,258,115 B1 | 7/2001 | Dubrul |
| 6,270,477 B1 | 8/2001 | Bagaoisan et al. |
| 6,277,139 B1 | 8/2001 | Levinson et al. |
| 6,306,163 B1 | 10/2001 | Fitz |
| 6,346,116 B1 | 2/2002 | Brooks et al. |

(56) References Cited

U.S. PATENT DOCUMENTS

| | | |
|---|---|---|
| 6,361,545 B1 | 3/2002 | Macoviak et al. |
| 6,364,894 B1 | 4/2002 | Healy et al. |
| 6,368,338 B1 | 4/2002 | Konya et al. |
| 6,391,044 B1 | 5/2002 | Yadav et al. |
| 6,454,741 B1 | 9/2002 | Muni et al. |
| 6,454,775 B1 | 9/2002 | Demarais et al. |
| 6,485,466 B2 | 11/2002 | Hamilton |
| 6,485,500 B1 | 11/2002 | Kokish et al. |
| 6,485,501 B1 | 11/2002 | Green |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,537,295 B2 | 3/2003 | Petersen |
| 6,540,768 B1 | 4/2003 | Diaz et al. |
| 6,551,302 B1 | 4/2003 | Rosinko et al. |
| 6,558,405 B1 | 5/2003 | McInnes |
| 6,569,148 B2 | 5/2003 | Bagaosian et al. |
| 6,579,484 B1 | 6/2003 | Tiernan et al. |
| 6,589,262 B1 | 7/2003 | Honebrink et al. |
| 6,596,011 B2 | 7/2003 | Johnson et al. |
| 6,610,077 B1 | 8/2003 | Hancock et al. |
| 6,616,681 B2 | 9/2003 | Hanson et al. |
| 6,620,148 B1 | 9/2003 | Tsugita |
| 6,695,865 B2 | 2/2004 | Boyle et al. |
| 6,702,834 B1 | 3/2004 | Boylan et al. |
| 6,773,448 B2 | 8/2004 | Kusleika et al. |
| 6,805,684 B2 | 10/2004 | Bonnette et al. |
| 6,805,692 B2 | 10/2004 | Muni et al. |
| 6,824,553 B1 | 11/2004 | Samson et al. |
| 6,866,669 B2 | 3/2005 | Buzzard et al. |
| 6,878,151 B2 | 4/2005 | Carrison et al. |
| 6,879,854 B2 | 4/2005 | Windheuser et al. |
| 6,911,036 B2 | 6/2005 | Douk et al. |
| 6,945,956 B2 | 9/2005 | Waldhauser et al. |
| 6,949,104 B2 | 9/2005 | Griffis et al. |
| 6,951,570 B2 | 10/2005 | Linder et al. |
| 6,958,059 B2 | 10/2005 | Zando-Azizi |
| 6,969,395 B2 | 11/2005 | Eskuri |
| 6,991,642 B2 | 1/2006 | Petersen |
| 6,995,858 B2 | 2/2006 | Murakami et al. |
| 7,052,500 B2 | 5/2006 | Bashiri et al. |
| 7,056,328 B2 | 6/2006 | Arnott |
| 7,115,134 B2 | 10/2006 | Chambers |
| 7,115,138 B2 | 10/2006 | Renati et al. |
| 7,166,120 B2 | 1/2007 | Kusleika |
| 7,220,271 B2 | 5/2007 | Clubb et al. |
| 7,229,431 B2 | 6/2007 | Houser et al. |
| 7,229,463 B2 | 6/2007 | Sutton et al. |
| 7,229,464 B2 | 6/2007 | Hanson et al. |
| 7,232,452 B2 | 6/2007 | Adams et al. |
| 7,285,126 B2 | 10/2007 | Sepetka et al. |
| 7,309,334 B2 | 12/2007 | von Hoffmann |
| 7,329,278 B2 | 2/2008 | Seguin et al. |
| 7,374,564 B2 | 5/2008 | Brown |
| 7,449,010 B1 | 11/2008 | Hayase et al. |
| 7,476,232 B2 | 1/2009 | Deal |
| 7,549,974 B2 | 6/2009 | Nayak |
| 7,625,207 B2 | 12/2009 | Hershey et al. |
| 7,736,355 B2 | 6/2010 | Itou et al. |
| 7,842,055 B2 | 11/2010 | Pintor et al. |
| 7,879,062 B2 | 2/2011 | Galdonik et al. |
| 7,938,820 B2 | 5/2011 | Webster et al. |
| 8,021,351 B2 | 9/2011 | Boldenow et al. |
| 8,048,032 B2 | 11/2011 | Root et al. |
| 8,092,483 B2 | 1/2012 | Galdonik et al. |
| 8,231,600 B2 | 7/2012 | von Hoffmann |
| 8,308,712 B2 | 11/2012 | Provost et al. |
| 8,419,786 B2 | 4/2013 | Cottone, Jr. et al. |
| 8,465,456 B2 | 6/2013 | Stivland |
| 8,764,813 B2 | 7/2014 | Jantzen et al. |
| 8,795,305 B2 | 8/2014 | Martin et al. |
| 8,814,892 B2 | 8/2014 | Galdonik et al. |
| 8,932,286 B2 | 1/2015 | Terry et al. |
| 9,199,057 B2 | 12/2015 | Nielsen |
| 9,433,427 B2 | 9/2016 | Look et al. |
| 9,523,792 B2 | 12/2016 | Seo et al. |
| 9,532,792 B2 | 1/2017 | Galdonik et al. |
| 9,993,613 B2 | 6/2018 | Wang et al. |
| 10,213,582 B2 | 2/2019 | Garrison et al. |
| 10,463,386 B2 | 11/2019 | Ogle et al. |
| 10,478,535 B2 | 11/2019 | Ogle |
| 10,518,066 B2 | 12/2019 | Pokorney et al. |
| 2001/0031980 A1 | 10/2001 | Wensel et al. |
| 2001/0044600 A1 | 11/2001 | Elkins |
| 2001/0044632 A1 | 11/2001 | Daniel et al. |
| 2001/0051811 A1 | 12/2001 | Bonnette et al. |
| 2002/0035347 A1 | 3/2002 | Bagaoisan et al. |
| 2002/0055747 A1 | 5/2002 | Cano et al. |
| 2002/0062133 A1 | 5/2002 | Gilson et al. |
| 2002/0095174 A1 | 7/2002 | Tsugita et al. |
| 2002/0111648 A1 | 8/2002 | Kusleika et al. |
| 2002/0123765 A1 | 9/2002 | Sepetka et al. |
| 2002/0133111 A1 | 9/2002 | Shadduck |
| 2002/0143362 A1 | 10/2002 | Mackoviak et al. |
| 2002/0151927 A1 | 10/2002 | Douk et al. |
| 2002/0165574 A1 | 11/2002 | Ressemann et al. |
| 2002/0169472 A1 | 11/2002 | Douk et al. |
| 2002/0183782 A1 | 12/2002 | Tsguita et al. |
| 2003/0023263 A1 | 1/2003 | Krolik et al. |
| 2003/0065353 A1 | 4/2003 | Horzewski et al. |
| 2003/0120208 A1 | 6/2003 | Houser et al. |
| 2003/0135232 A1 | 7/2003 | Douk et al. |
| 2003/0191492 A1 | 10/2003 | Gellman et al. |
| 2004/0006344 A1 | 1/2004 | Nguyen et al. |
| 2004/0006365 A1 | 1/2004 | Brady et al. |
| 2004/0015151 A1 | 1/2004 | Chambers |
| 2004/0153118 A1 | 8/2004 | Clubb et al. |
| 2004/0220611 A1 | 11/2004 | Ogle |
| 2004/0254602 A1 | 12/2004 | Lehe et al. |
| 2005/0004553 A1 | 1/2005 | Douk |
| 2005/0021075 A1 | 1/2005 | Bonnette et al. |
| 2005/0021152 A1 | 1/2005 | Ogle et al. |
| 2005/0075661 A1 | 4/2005 | Levine et al. |
| 2005/0085847 A1 | 4/2005 | Galdonik et al. |
| 2005/0107738 A1 | 5/2005 | Slater et al. |
| 2005/0154344 A1 | 7/2005 | Chang |
| 2005/0209631 A1 | 9/2005 | Galdonik et al. |
| 2005/0228479 A1 | 10/2005 | Pavcnik et al. |
| 2005/0245894 A1 | 11/2005 | Zando-Azizi |
| 2005/0277976 A1 | 12/2005 | Galdonik et al. |
| 2006/0030876 A1 | 2/2006 | Peacock, III et al. |
| 2006/0047301 A1 | 3/2006 | Ogle |
| 2006/0129091 A1 | 6/2006 | Bonnette et al. |
| 2006/0195137 A1 | 8/2006 | Sepetka et al. |
| 2006/0200047 A1 | 9/2006 | Galdonik et al. |
| 2006/0200191 A1 | 9/2006 | Zando-Azizi |
| 2007/0005002 A1 | 1/2007 | Millman et al. |
| 2007/0060908 A1 | 3/2007 | Webster et al. |
| 2007/0060911 A1 | 3/2007 | Webster et al. |
| 2007/0060944 A1 | 3/2007 | Boldenow et al. |
| 2007/0135733 A1 | 6/2007 | Soukup et al. |
| 2007/0135832 A1 | 6/2007 | Wholey |
| 2007/0185501 A1 | 8/2007 | Martin et al. |
| 2007/0197956 A1 | 8/2007 | Le et al. |
| 2007/0227543 A1 | 10/2007 | Peichel |
| 2007/0250040 A1 | 10/2007 | Provost et al. |
| 2007/0250096 A1 | 10/2007 | Yamane et al. |
| 2007/0260115 A1 | 11/2007 | Brock et al. |
| 2007/0287956 A1 | 12/2007 | Tal |
| 2008/0086110 A1 | 4/2008 | Galdonik et al. |
| 2008/0109088 A1 | 5/2008 | Galdonik et al. |
| 2008/0172066 A9 | 7/2008 | Galdonik et al. |
| 2009/0076319 A1 | 3/2009 | Muyari |
| 2009/0131970 A1 | 5/2009 | Chanduszko et al. |
| 2009/0270895 A1* | 10/2009 | Churchill ............... A61B 1/303 606/170 |
| 2010/0204672 A1 | 8/2010 | Lockhart et al. |
| 2010/0211050 A1 | 8/2010 | Luther |
| 2010/0280451 A1 | 11/2010 | Teeslink et al. |
| 2011/0093000 A1 | 4/2011 | Ogle et al. |
| 2011/0172678 A1 | 7/2011 | Behl et al. |
| 2012/0123466 A1 | 5/2012 | Porter et al. |
| 2012/0253313 A1 | 10/2012 | Galdonik et al. |

(56) References Cited

U.S. PATENT DOCUMENTS

| | | |
|---|---|---|
| 2013/0184742 A1 | 7/2013 | Ganesan et al. |
| 2013/0225937 A1 | 8/2013 | Schaeffer et al. |
| 2013/0317409 A1 | 11/2013 | Cully et al. |
| 2014/0018773 A1 | 1/2014 | Wang et al. |
| 2014/0114335 A1 | 4/2014 | Banko |
| 2014/0117397 A1 | 5/2014 | Saeki et al. |
| 2014/0155980 A1 | 6/2014 | Turjman et al. |
| 2014/0163489 A1* | 6/2014 | Walti ............ A61M 1/784 422/292 |
| 2014/0249508 A1 | 9/2014 | Wang et al. |
| 2014/0276537 A1 | 9/2014 | Kruse |
| 2015/0018937 A1 | 1/2015 | Lagodzki et al. |
| 2015/0173782 A1 | 6/2015 | Garrison et al. |
| 2015/0209066 A1 | 6/2015 | Dahm et al. |
| 2015/0216650 A1 | 8/2015 | Shaltis |
| 2015/0282821 A1 | 10/2015 | Look et al. |
| 2015/0327919 A1 | 11/2015 | Clopp et al. |
| 2016/0066931 A1 | 3/2016 | Kugler et al. |
| 2016/0166754 A1 | 6/2016 | Kassab et al. |
| 2016/0199620 A1 | 7/2016 | Pokorney et al. |
| 2016/0220741 A1 | 8/2016 | Garrison et al. |
| 2016/0270806 A1 | 9/2016 | Wallace |
| 2017/0056032 A1 | 3/2017 | Look et al. |
| 2017/0056061 A1 | 3/2017 | Ogle et al. |
| 2017/0143938 A1 | 5/2017 | Ogle et al. |
| 2017/0181760 A1 | 6/2017 | Look et al. |
| 2017/0203036 A1 | 7/2017 | Mazlish et al. |
| 2017/0231647 A1 | 8/2017 | Saunders et al. |
| 2017/0239447 A1 | 8/2017 | Yang et al. |
| 2017/0252051 A1 | 9/2017 | Wan et al. |
| 2017/0252057 A1 | 9/2017 | Bonnette et al. |
| 2017/0290598 A1* | 10/2017 | Culbert ............ A61M 25/0026 |
| 2017/0290600 A1 | 10/2017 | Ulm, III |
| 2017/0303942 A1 | 10/2017 | Greenhalgh et al. |
| 2017/0303948 A1 | 10/2017 | Wallace et al. |
| 2017/0333060 A1 | 11/2017 | Panian |
| 2017/0333237 A1 | 11/2017 | Walzman |
| 2017/0354427 A1 | 12/2017 | Bonnette et al. |
| 2018/0008295 A1 | 1/2018 | Ulm, III |
| 2018/0064453 A1 | 3/2018 | Garrison et al. |
| 2018/0161541 A1 | 6/2018 | Haldis et al. |
| 2018/0339130 A1 | 11/2018 | Ogle |
| 2019/0117891 A1 | 4/2019 | Carothers et al. |
| 2019/0183517 A1 | 6/2019 | Ogle et al. |

FOREIGN PATENT DOCUMENTS

| | | |
|---|---|---|
| CN | 107260252 A * | 10/2017 |
| EP | 0117940 A2 | 9/1948 |
| EP | 1226795 A2 | 7/2002 |
| GB | 2020557 A | 11/1979 |
| WO | 95-05209 A1 | 2/1995 |
| WO | 98-38930 A1 | 9/1998 |
| WO | 00-16705 A1 | 3/2000 |
| WO | 02-055146 A1 | 7/2002 |
| WO | 02-085092 A2 | 10/2002 |
| WO | 2010-014777 A1 | 2/2010 |
| WO | 2017-091554 A1 | 6/2017 |

OTHER PUBLICATIONS

Penumbra, Inc., "Penumbra, Inc. Completes Pivotal Stroke Trial of Intracranial Revascularization" Press Release (2007).

Penumbra, Inc., "The Penumbra Pivotal Stroke Trial: Safety and Effectiveness of a New Generation of Mechanical Devices for Clot Removal in Intracranial Large Vessel Occlusive Disease," Stroke, 40:2761-2768 (2009).

Penumbra, Inc., "The Penumbra System®: Continuous Aspiration Thrombectomy (CAT)," Marketing Brochure © 2010 (6 pages).

Penumbra, Inc., "5Max™: Direct Aspiration™ Enables Choice," Marketing brochure © 2013 (6 pages).

Reeder et al., "Aspiration Thrombectomy for Removal of Coronary Thrombosis," American Journal of Cardiology, 70:107-110 (Jul. 1, 1992) (Abstract only).

Webb et al., "Retrieval and Analysis of Particulate Debris After Saphenous Vein Graft Intervention," Journal of the American College of Cardiology, 34(2);468-475 (1999).

Yoo et al., "The Penumbra Stroke System: a technical review," Journal of NeuroInterventional Surgery, 4:199-205 (2012).

Abstracts from the 2007 International Stroke Conference, Stroke, 38(2):453-607 (2007).

International Search Report and Written Opinion from co-pending application, PCT/US2018/034197, dated Jul. 30, 2018 (12 pages).

European Search Report from co-pending application 18806441.4, for PCT/US2018/034197, dated Feb. 2, 2021.

* cited by examiner

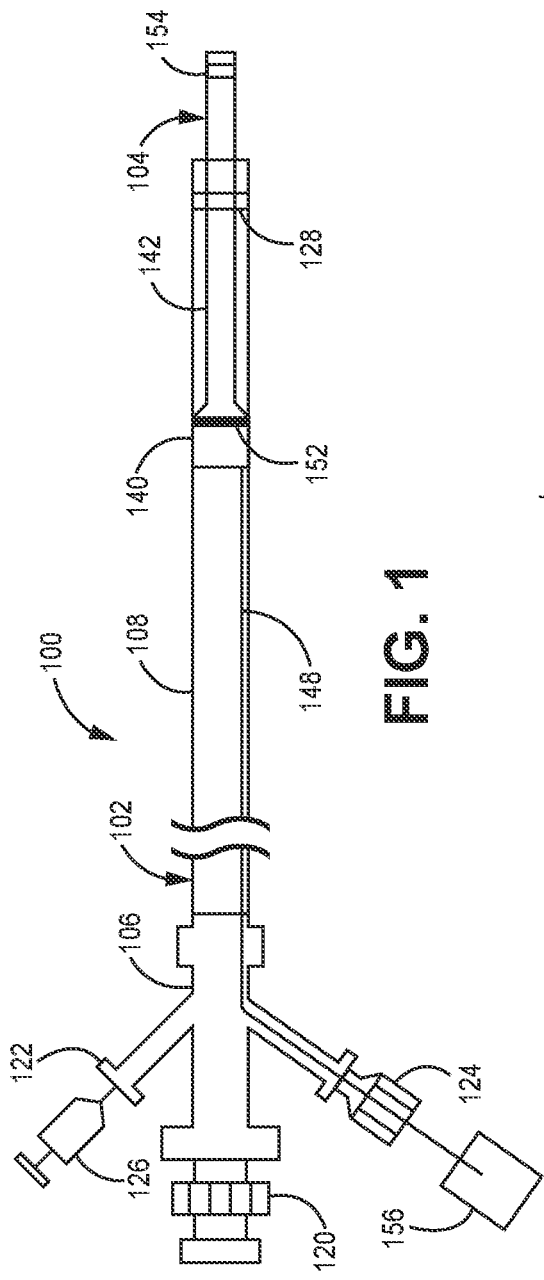
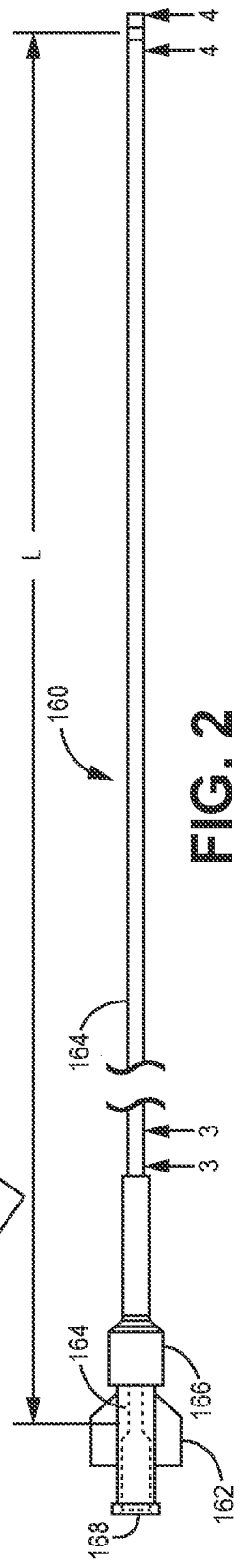
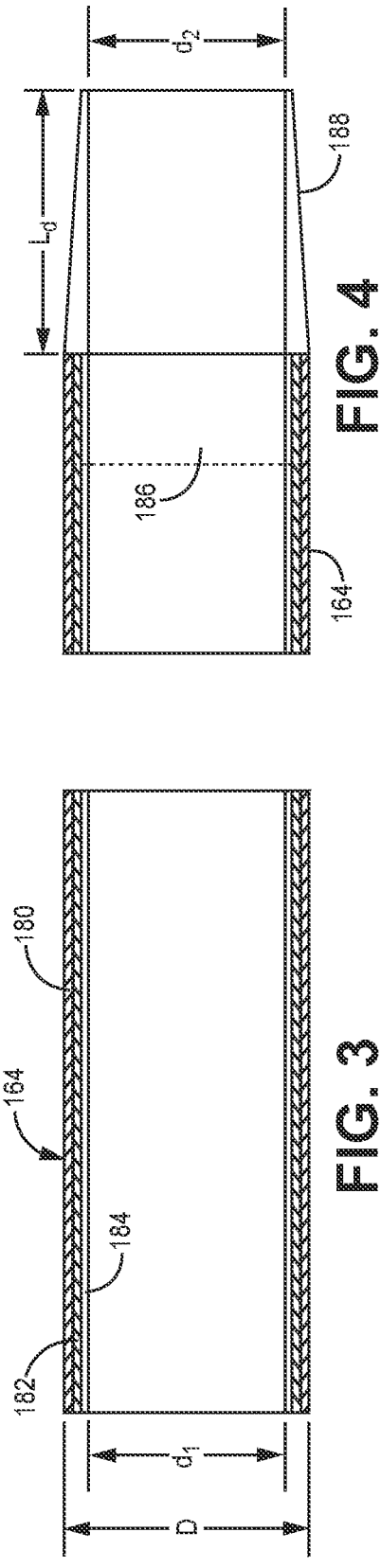

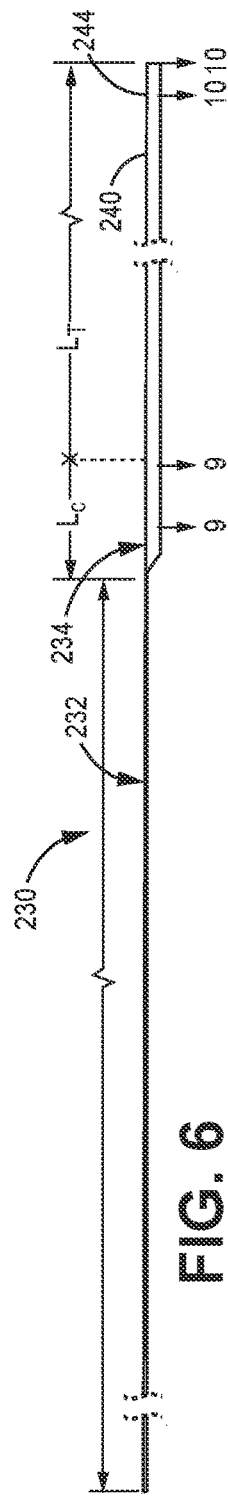
FIG. 6
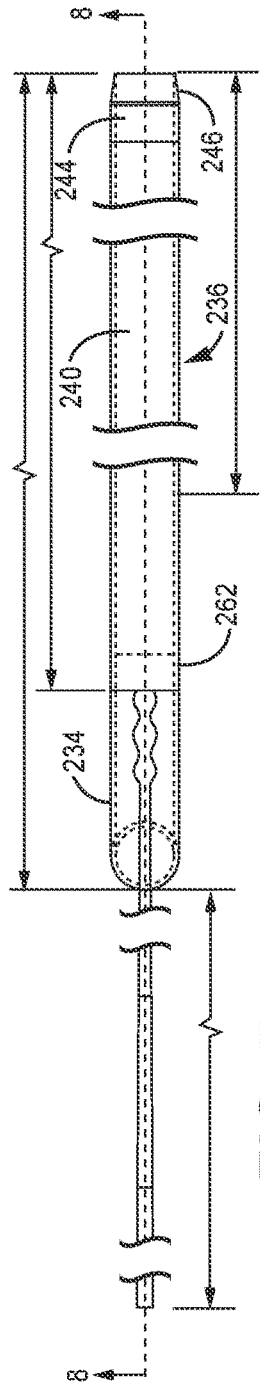
FIG. 7
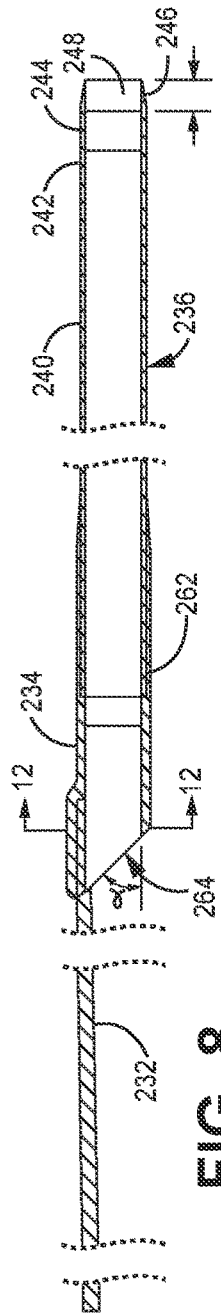
FIG. 8
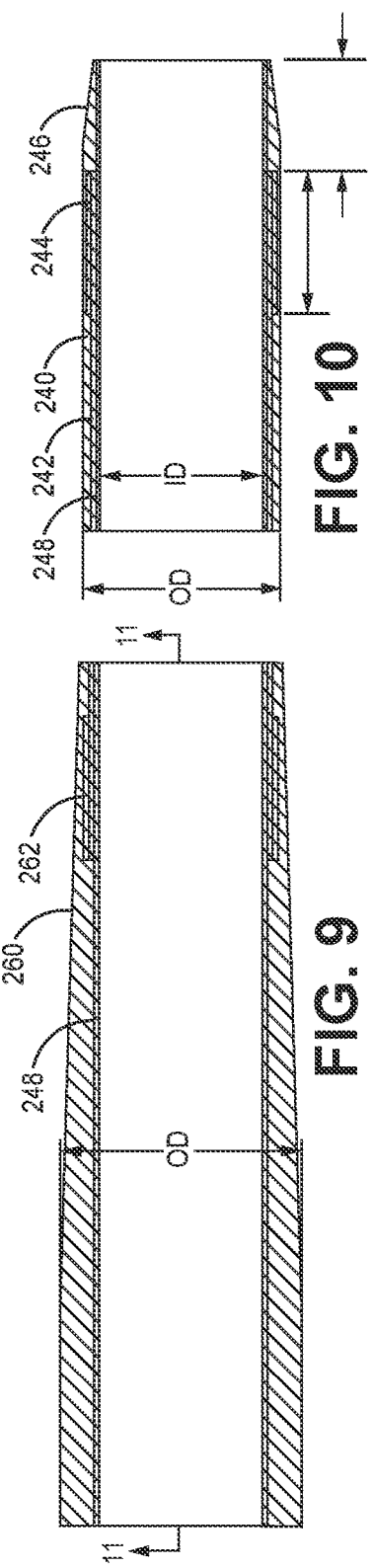
FIG. 9
FIG. 10

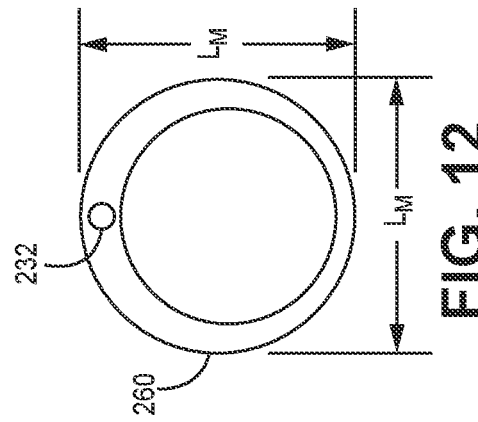
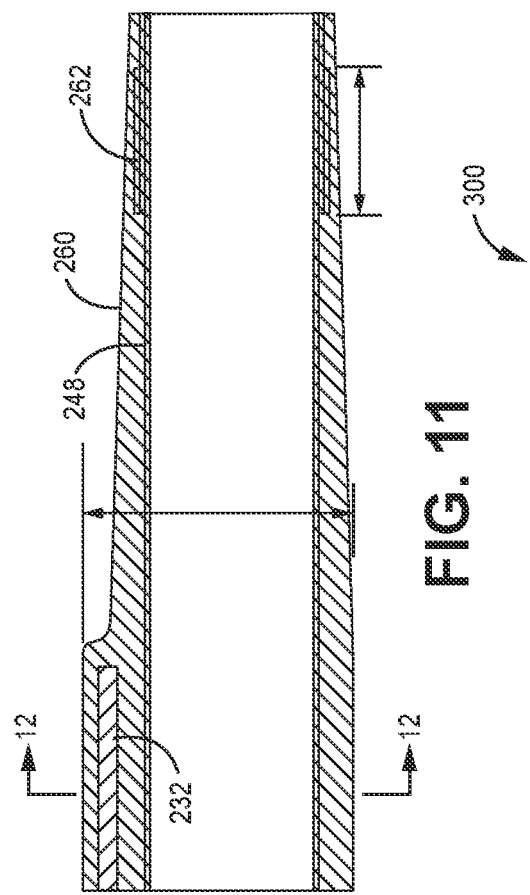
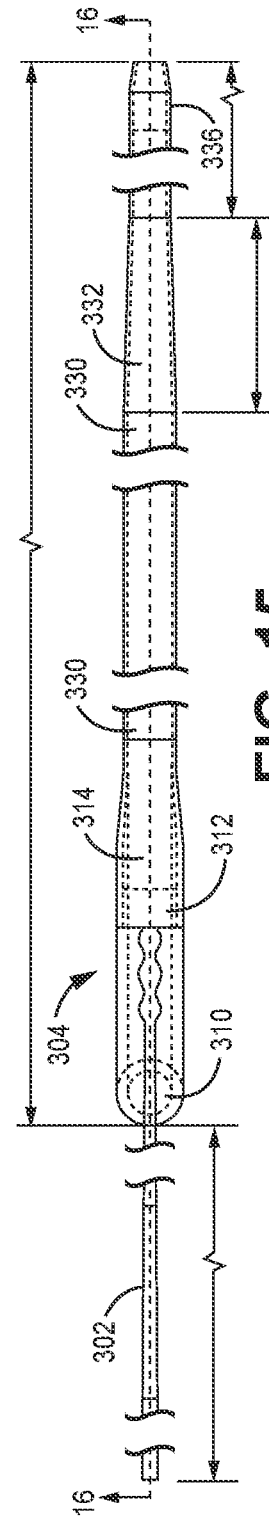
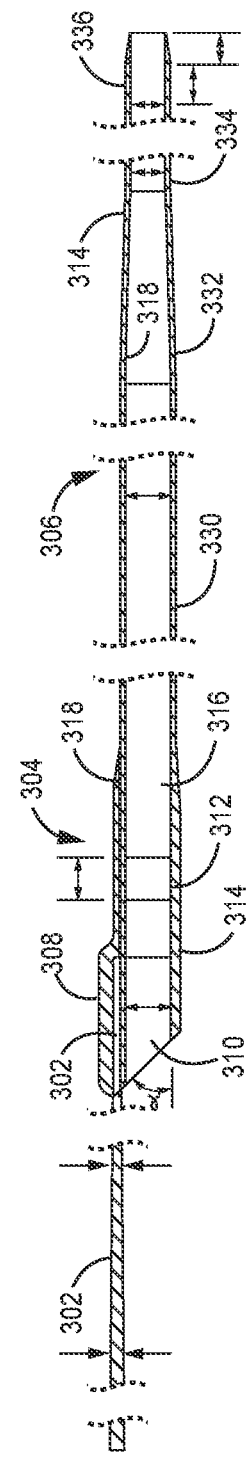
FIG. 11
FIG. 12
FIG. 15
FIG. 16

SUCTION CATHETER SYSTEMS FOR APPLYING EFFECTIVE ASPIRATION IN REMOTE VESSELS, ESPECIALLY CEREBRAL ARTERIES

CROSS REFERENCE TO RELATED APPLICATIONS

This application is a continuation of copending U.S. patent application Ser. No. 15/848,146 to Ogle, filed Dec. 12, 2017, entitled "Suction Catheter Systems for Applying Effective Aspiration in Remote Vessels, Especially Cerebral Arteries," incorporated herein by reference.

FIELD OF THE INVENTION

The invention relates to catheters designed for use in bodily vessels with tortuous paths, such as cerebral arteries. In particular, the invention relates to suction catheter systems comprising a guide catheter and a suction extension slidably disposed within the guide catheter.

BACKGROUND OF THE INVENTION

Procedures in blood vessels of the brain are gaining use as an approach for ameliorating acute stroke events or other interventions in blood vessels in the brain. Blood vessels in the brain follow particularly tortuous paths which can increase the difficulty of reaching target locations in these vessels. Other vessels in a patient can also follow winding paths that increase the difficulty of reaching target locations.

Aspiration catheters have found use with respect to removal of clots from vessels. Furthermore, a significant reason for ischemic injury during percutaneous procedures can be generation of emboli that block smaller distal vessels. Aspiration catheters used alone or with embolic protection device can be effective to capture emboli generated during procedures. The delivery of effective devices to the small blood vessels of the brain to remove clots and/or to capture emboli remains challenging.

Ischemic strokes can be caused by clots within a cerebral artery. The clots block blood flow, and the blocked blood flow can deprive brain tissue of its blood supply. The clots can be thrombus that forms locally or an embolus that migrated from another location to the place of vessel obstruction. To reduce the effects of the cut off in blood supply to the tissue, time is an important factor. In particular, it is desirable to restore blood flow in as short of a period of time as possible. The cerebral artery system is a highly branched system of blood vessels connected to the interior carotid arteries. The cerebral arteries are also very circuitous. Medical treatment devices should be able to navigate along the circuitous route posed by the cerebral arteries for placement into the cerebral arteries.

SUMMARY OF THE INVENTION

In a first aspect, the invention pertains to a method for removing thrombus from a patient's vessel using a suction catheter system comprising: proximal fittings comprising a hemostatic valve; a guide catheter with a distal end and a proximal end connected to the proximal fittings; and a suction extension comprising a tubular extension with a distal end and a proximal end, a connecting section at the proximal end of tubular extension, and a control structure extending in a proximal direction from the tubular extension. The method can comprise delivering suction through a suction lumen extending from the distal end of the tubular extension to the proximal end of the guide catheter with the distal end of the tubular extension extending from the distal end of the guide catheter. Generally, for at least a portion of the time of delivery of suction, the connecting section is within the guide catheter, and the control structure extends from the proximal end of the guide catheter. The method can also comprise withdrawing the tubular extension from the guide catheter lumen during delivery of negative pressure in the suction lumen from the proximal fittings, in which the connecting section is withdrawn into the proximal fittings distal to the hemostatic valve such that a suction lumen then extends fully along a lumen of the guide catheter.

In a further aspect, the invention pertains to a suction catheter system comprising a guide catheter having a tubular shaft with a central lumen having, a proximal end and a distal opening, a suction extension, and proximal fittings. The suction extension can comprise a connecting section with a central lumen, a tubular extension, and a control structure. The tubular extension can comprise a tube that is connected with the connecting section and extends from the connecting section in a distal direction to form a continuous lumen through the central lumen of the connecting section through the tube of the tubular extension, and the control structure can comprise an elongated structure extending from the connecting section in a proximal direction. The connecting section can be configured to slide within at least a portion of the central lumen of the guide catheter to change the relative position of the connecting section within the central lumen and provide for at least a portion of tubular extension to extend outward from the distal opening of the tubular shaft at appropriate configurations of the connecting section. The proximal fittings generally can be connected to the proximal end of the guide catheter and can comprise a branched manifold with at least one branch having a hemostatic valve and a tubular segment to provide a length between the hemostatic valve and the proximal end of the tubular shaft of the guide catheter that is at least as long as the length of the tube of the suction extension.

In another aspect, the invention pertains to a suction catheter system comprising a guide catheter comprising a tubular shaft with a central lumen, and having a proximal end and a distal opening, a suction extension, and proximal fittings. The suction extension can comprise a connecting section with a central lumen, a tubular extension, and a control structure. The tubular extension can comprise a tube that is connected with the connecting section and extends from the connecting section in a distal direction, and the control structure can comprise an elongated structure extending from the connecting section in a proximal direction. Generally, the connecting section can be configured to slide within at least a portion of the central lumen of the guide catheter to change the relative position of the connecting section within the central lumen and to provide for at least a portion of tubular extension to extend outward from the distal opening of the tubular shaft at appropriate configurations of the connecting section. The proximal fittings can comprise a branched manifold with at least one branch having a hemostatic valve, and with a pressure sensor configured to measure the pressure in the proximal fittings. Generally, the proximal fittings are connected to the proximal end of the guide catheter.

In an additional aspect, the invention pertains to a method for removing thrombus from a patient's vessel using a suction catheter system comprising proximal fittings comprising a hemostatic valve and a pressure sensor configured to measure the pressure in the proximal fittings; a guide catheter with a distal end and a proximal end connected to the proximal fittings; and a section extension. The suction extension can comprise a tubular extension with a distal end, a connecting section at the proximal end of tubular extension, and a control structure extending in a proximal direction from the tubular extension. In some embodiments, the method comprises delivering suction through a suction lumen extending from the distal end of the tubular extension to the proximal end of the guide catheter, in which the distal end of the tubular extension extends from the distal end of the guide catheter, the connecting section is within the guide catheter, and the control structure extends from the proximal end of the guide catheter. The method can further comprise monitoring the pressure in the proximal fittings at least one time during the delivery of suction.

In other aspects, the invention pertains to a suction catheter system comprising a guide catheter and a suction extension. The guide catheter can comprise a tubular shaft with a central lumen having, a proximal end and a distal opening, and a proximal section operably connected with the proximal end of the tubular shaft and having fittings that connect to a suction device, wherein the tubular shaft comprises an engagement section having an inner diameter associated with the lumen extending through the engagement section. The suction extension can comprise a connecting section with a central lumen, a tubular extension comprising a tube that is connected with the tubular element of the connecting portion extends from the connecting portion in a distal direction, and a control structure comprising an elongated structure extending from the connecting section in a proximal direction. In some embodiments, at least a portion of the connecting section has a non-cylindrical cross section with a major outer diameter and a minor outer diameter smaller than the major outer diameter. The tubular extension can have a distal inner diameter that is from about 20 percent to about 90 percent of the guide catheter central lumen inner diameter, wherein the connecting section is configured to slide within the central lumen of the engagement section of the tubular shaft to change the relative position of the connecting section within the central lumen and provide for at least a portion of the suction extension to extend outward from the distal opening of the tubular shaft at appropriate configurations of the connecting section. In some embodiments, a suction lumen is formed extending from the fitting configured to connect to the suction device through a portion of the central lumen, the connecting section and the tubular extension to a distal opening of the tubular extension, and the connecting section engages the inner lumen of the engagement section of the guide catheter at two locations along the circumference.

Additionally, the invention pertains to a suction catheter system comprising a guide catheter and a suction extension. The guide catheter can comprise a tubular shaft with a central lumen having, a proximal end and a distal opening, and a proximal section operably connected with the proximal end of the tubular shaft and having fittings that connect to a suction device. The tubular shaft can comprise an engagement section having an inner diameter associated with the lumen extending through the engagement section, and a distal section having an inner diameter that is from about 0.034 mm to about 0.25 mm less than the inner diameter of the engagement section and the distal section having a length from about 1 mm to about 50 mm. The suction extension can comprise a connecting section with a lumen and with an average outer diameter greater by at least 0.025 mm than the inner diameter of the distal section of the tubular shaft, a tubular extension comprising a tube that is connected with the connecting section and extends from the connecting section in a distal direction, and a control structure comprising an elongated structure and extending from the connecting section in a proximal direction. The tubular extension can have a distal most inner diameter that is from about 20 percent to about 90 percent of the engagement section inner diameter, and the connecting section can be configured to slide within the central lumen of the engagement section to change the relative position of the connecting section within the central lumen and provide for at least a portion of the tubular extension to extend outward from the distal opening of the tubular shaft at appropriate configurations of the connecting section. Generally, a suction lumen is formed extending from the fitting configured to connect to the suction device through a portion of the central lumen, the connecting section and the tubular extension to a distal opening with the suction extension slidably positioned with the connecting section within the lumen of the engagement section of the tubular shaft with the tubular extension extending through and extending outward in a distal direction from the distal section of the tubular shaft.

BRIEF DESCRIPTION OF THE DRAWINGS

FIG. 1 is a side view of a suction catheter system comprising a guide catheter with a suction extension with the guide catheter shown as transparent to allow visualization of structure within the guide catheter.

FIG. 2 is a side view of an embodiment of a guide catheter extending from a luer fitting to a distal tip.

FIG. 3 is a fragmentary sectional view of a portion of the guide catheter of FIG. 2 between points 3-3 in FIG. 2 with the cross section taken along a plane through the central axis of the catheter.

FIG. 4 is a fragmentary sectional view of a portion of the guide catheter of FIG. 2 between points 4-4 in FIG. 2 with the cross section taken along a plane through the central axis of the catheter.

FIG. 6 is a side view of an embodiment of a section extension.

FIG. 7 is a top view of the suction extension of FIG. 6 with some hidden structure shown with dashed lines.

FIG. 8 is a sectional side view of the suction extension of FIG. 6 taken along line 8-8 of FIG. 7.

FIG. 9 is a fragmentary sectional view taken along line 9-9 of FIG. 6.

FIG. 10 is a fragmentary sectional view taken along line 10-10 of FIG. 6.

FIG. 11 is a fragmentary sectional view of the catheter of FIG. 11 taken along an orthogonal view indicated by line 11-11 of FIG. 9.

FIG. 12 is a sectional end view of the catheter of FIG. 6 taken along line 12-12 of FIG. 8.

FIG. 15 is a top view of an alternative embodiment of a suction extension in which a tubular extension has two tubular sections with different diameters connected by a taper section.

FIG. 16 is a sectional view of the alternative embodiment of the suction extension shown in FIG. 15, in which the section is taken along line 16-16 of FIG. 15.

DETAILED DESCRIPTION OF THE INVENTION

Figure 5:
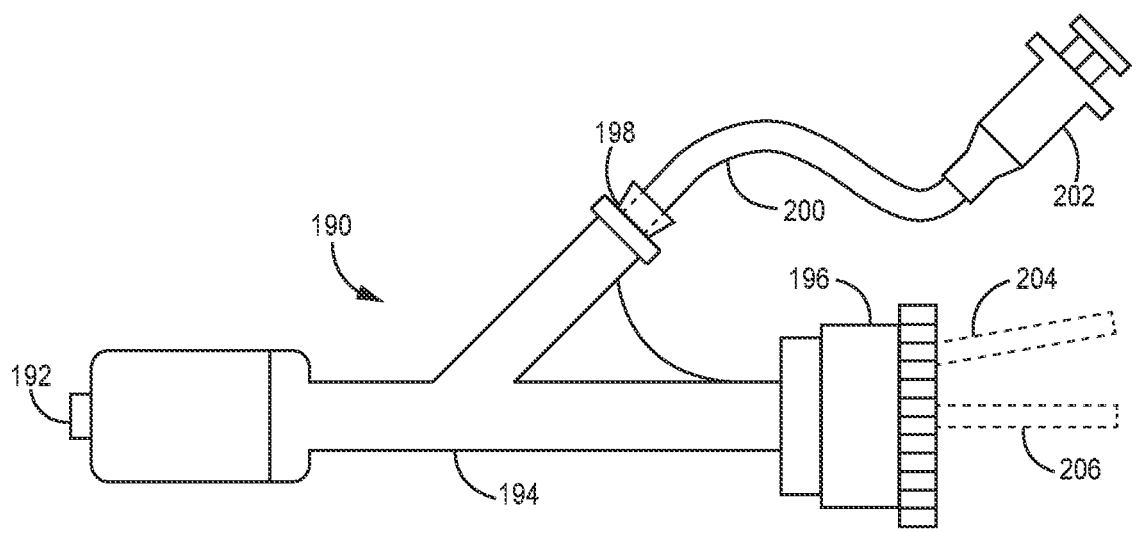
FIG. 5 is a side view of a branched hemostatic valve fitting suitable for connection with the luer fitting of the guide catheter of FIG. 2.

A suction catheter system can include a guide catheter adapted with a suction extension having a narrower distal tube that can provide suction with a high flow rate. In some embodiments, the suction extension has a connecting section that has an asymmetric circumference interfacing with the inner surface of the guide catheter with contact at two locations to provide an effective fluid seal while providing for translation of the suction extension within the guide catheter. In alternative or additional embodiments, the guide catheter can have a distal portion of a tubular element that has a narrower diameter that effectively limits the movement of the suction extension in a distal direction. Proximal fittings can be provided in some embodiments to allow withdrawal of the tubular portion (tubular extension) of the suction extension from the guide catheter without bringing the tubular extension of the suction extension through a hemostatic valve. Methods are described for the use of the suction catheter system such that the tubular extension of the suction extension that provides part of the aspiration lumen remains in a sealed configuration with respect to the guide catheter lumen, in some embodiments, for the entire period in which the guide catheter is within a patient Improved processing can be guided through the use of real time line pressure measurements with a pressure transducer associated with appropriate back end tools. Suction catheters can be used advantageously for the removal of thrombus and emboli from bodily vessels, such as arteries. Some vessels can have a narrow diameter, and treatment locations can be downstream along a circuitous path, and for such vessels there are constraints on the catheter structures able to reach the treatment locations in the vessel.

The designs described herein comprise a slidable suction extension that can be adapted for use in conjunction with a corresponding guide catheter, which forms a significant portion of the overall suction lumen when suction extension is deployed from the distal end of the guide catheter. While the suction catheter system can be used in any suitable vessels of the body, the system can be particularly desirable in cerebral blood vessels, such as for the treatment of acute stroke. The suction catheter system can be effectively used as a standalone suction catheter for thrombus removal. Furthermore, the suction catheter system can be effective as a component of a thrombectomy treatment system or other medical system to provide suction with the use of other medical devices, such as a clot engagement device, to disrupt thrombus and/or a filter structure that can catch emboli generated in the procedure as well as to be used to pull toward the suction catheter system. The treatment system can be effectively designed for stroke treatment.

Less invasive procedures, which are commonly referred to in the art as minimally invasive procedures, are desirable in the medical context when appropriate to reduce patient recovery times and in many cases to improve outcomes. In particular, less invasive procedures are commonly performed in the vasculature using catheter based system for reaching remote locations in a selected blood vessel for the performance of various treatment processes. These procedures can also be referred to as percutaneous procedures or transluminal procedures, in contrast with open surgical procedures, to emphasize the delivery through a vessel lumen. The discussion herein focuses on treatment of ischemic stroke since the devices can be particularly effective to treat these clinically important conditions, although the devices can be used in other procedures both in the vasculature and other bodily vessels. Patients include humans and can include other mammals, such as pet animals and farm animals. The terms proximal and distal are used in their conventional sense in the art, i.e., proximal refers to closer to the point of entry into the patient along the path in the vasculature or other vessel and distal refers to farther from the point of entry along the path in the vasculature.

A slidable suction extension generally comprises a connecting section that engages the inner wall of the guide catheter to make a suitably tight fit. The connecting section generally links a control structure, such as a control wire, extending in a proximal direction from the connecting section, and a tubular extension that extends from the control structure in a distal direction. The control structure generally extends outside of the patient to provide for positioning the suction extension with its distal tip near a treatment location in a blood vessel. The tubular extension, which may have an optional curved tip, can be tracked well over a guidewire to reach difficult to reach locations in a vessel.

Since thrombus can be held at the distal tip of the suction extension during the application of suction to remove the clot form the vessel, it can be desirable to withdraw a tubular extension of the suction extension into the guide catheter with the application of suction to reduce the chance of embolization of thrombus and loss of emboli that can travel upstream in the vessels. To further reduce the risk of embolization, it can be desirable to fully remove the tubular extension from the guide catheter with the application of suction prior to removal of the guide catheter from the patient. Desirable proximal fittings at the back end of the catheter system are described that allow for the removal of the tubular extension from the guide catheter without passing the tubular extension of the suction extension through a hemostatic valve. Since the proximal end of the tubular extension generally is open, passage of the proximal end of the tubular extension through a hemostatic valve can expose the interior lumen of the tubular extension and potentially of the guide catheter to the ambient environment.

Suitable proximal fittings suitable for withdraw the tubular extension have a tubular extension following a branch structure in which the tubular extension has sufficient length to hold the suction extension within the isolated region behind a hemostatic valve but external to the tubular element of the guide catheter. Several suitable configurations are described below and other configurations can follow from the discussion of these embodiments. It can be noted that aspiration is generally applied from a separate branch of the fittings and that multiple branches can be provided in the overall manifold, which may or may not have separable components that are assembled for use.

The measurement of the pressure in the proximal fittings can provide valuable information relative to the procedure. Potential structures for placement of the pressure sensor are discussed below. If the pressure is near zero in the proximal fittings, then the flow in the line to the pump is effectively unconstrained. It is observed that pressure with flow passing through the suction extension results in a measurable drop in pressure but still at a pressure significantly less than the pump pressure. If the suction extension is clogged with thrombus or if the suction extension is kinked, the measured pressure can approximate the pump pressure, which generally indicates that flow is essentially block within the catheter. Knowledge of the blockage can be used to significantly improve the procedure with respect to efficacy and safety. For example, if the blockage occurs early in the procedure, this may suggest kinking. Blockage later in the procedure can suggest blockage of the catheter with trapped thrombus, which generally instructs that contrast dye or other infusion liquids should not be delivered through the catheter since the pressure of delivery can thrust the thrombus, which had been blocking the catheter, deeper into the vasculature. A pressure transducer can be introduced in alternative ways. For example, a pressure transducer can be placed along the inner wall of a fitting of the manifold or on a tube connected to the fittings with a configuration to provide pressure measurements. The pressure sensor may or may not be sterile depending on the location.

For the treatment of strokes, treatment devices can be advanced through arteries to blood vessels of the brain. Blood vessels generally relevant for acute stroke treatment are downstream in the blood flow from the internal carotid arteries, and arteries generally branch and decrease in average diameter as the vessel proceeds in a downstream direction in the arterial vasculature. The body has a right internal carotid artery and a left internal carotid artery. For convenience, the blood vessels downstream from the internal carotid arteries are referred to herein as cerebral arteries. The cerebral arteries can be accessed with catheter based systems from, for example, a femoral artery in the groin, an artery in the arm, or the carotid artery in the neck using hemostatic procedures and appropriate fittings, such as those known in the art. The cerebral arteries are known to follow circuitous paths, and complications in tracking devices along the vessels also follows due to narrow diameters and branching of the vessels as well as potentially dangerous risks from damage to the blood vessel that can cause a hemorrhagic stroke condition. Nevertheless, it can be desirable to access tortuous narrow arteries for stroke treatment. The devices described herein are designed for advantageous use in these tortuous narrow cerebral vessels, but a person of ordinary skill in the art will recognize utility of these devices in other medical procedures.

The present suction catheter systems incorporate guide catheters adapted with a slidable suction extension suitable for cerebral procedures. In vascular procedures generally, a guide catheter can be used to facilitate the delivery of therapeutic devices while allowing for more rapid, accurate delivery with less risk to vessel walls through providing a protected channel leading most of the way to the treatment site. In the cerebral procedures, a guide catheter can be placed from exterior of the patient at the point of entry into the vasculature with the distal end of the guide catheter in a carotid artery or interior carotid artery. Thus, a guide catheter can provide a lumen to a location relatively near to a treatment site. In some embodiments, conventional guide catheters can be used to assemble the desired suction catheter systems, but in other embodiments, specific guide catheter designs are used to form the suction catheter system. The size of the guide catheter sets limits on the diameter of treatment structures delivered to the treatment site, but this is generally not a significant issue since extendable devices can be delivered in a lower profile configuration with subsequent deployments to an extended configuration and since the vessel sizes generally decrease in a distal direction from the guide catheter limiting the need for larger treatment devices. The suction devices described herein provide a suction extension that can protrude from the distal end of the guide catheter an adjustable amount through the positioning of a connecting section of the suction extension interfacing the suction extension with the interior walls of the lumen of the guide catheter. The connecting section can make a sufficiently tight seal with the guide catheter walls such that suction in the guide catheter lumen is transmitted along the lumen of the suction extension. Desirable degrees of suction can be obtained through the suction extension using suction applied at the proximal end of the guide catheter.

The suction extension generally comprises a connecting section, a control structure extending in a proximal direction from the connecting section, and a tubular extension extending in a distal direction from the connecting section. The suction extension generally interfaces with the guide catheter and can be designed to be positioned with its tip at a selected position distal to the guide catheter for the performance of a procedure at a selected location, such as near the location of thrombus occluding a cerebral vessel. Since the relative position of the treatment location and the distal end of the guide catheter generally vary for a specific medical situation, the degree in which the suction extension extends from the guide catheter can be adjusted through relative movement of the suction extension using the control structure, e.g. a control wire. The suction extension should move within the guide catheter lumen without the need for excessive force, which may be facilitated through the use of low friction polymers on one or both adjacent surfaces.

The connecting section of the suction extension provides for an interface with the inner wall of the guide catheter to prevent most or all flow around the connecting section that does not flow through the lumen of the suction extension while keeping at least a portion of the connecting section within the guide catheter and while providing for appropriately unproblematic sliding of the suction extension relative to the guide catheter within the patient's vasculature. Various embodiments of components forming such an interface are discussed in published U.S. patent application 2017/0143938A1 to Ogle et al. (hereinafter the '938 application), entitled "Catheter Systems for Applying Effective Suction in Remote Vessels and Thrombectomy Procedures Facilitated by Catheter Systems," incorporated herein by reference. As described herein, a connecting section, referred to as a proximal portion in the '938 application, is described with a non-cylindrical cross sectional shape. Such a non-cylindrical cross sectional shape advantageously provides for contact with the guide catheter at two locations around the circumference along with a small clearance around the remaining section of the circumference of the connecting section. Contact with the inner lumen of the guide catheter applies some force on the connecting section that partially rounds out the circumference. This non-cylindrical shape for the connecting section allows for effective blockage of flow between the guide catheter wall and the connecting section while not inhibiting movement of the connecting section longitudinally to position the tip of the suction extension within the vasculature.

The non-circular cross sectional shape of the connecting section of the suction extension can generally be described as oval. The oval can be characterized at least in part by a major axis along the longer dimension of the oval and a minor axis along the shorter dimension of the oval orthogonal to the longer dimension. The connecting section can then contact or approach very closely to the inner surface of the engagement section of the guide catheter at two locations associated with the points along the circumference associated with the major axis. Correspondingly, the non-circular cross section can be characterized by an average radius, and the average radius can provide an overall very small clearance with the guide catheter while still providing for desirable function.

To form the non-circular cross section, a bump can be formed through the connection of a control wire along a surface of the connecting section along with extra polymer that provides for the desired shape along with reinforcing the control wire connection with the connecting section. Additional embodiments of the connecting section structure with an oval cross section are described below. Thus, the non-circular shape of the connecting section cross section can be designed for its interface with the guide catheter consistently with the overall structure of the suction extension.

Also, since it is desirable to prevent the connecting section of the suction extension from exiting from the distal end of the guide catheter, the suction extension and/or catheter can be designed to limit the distal movement of the suction extension. In an embodiment described herein, a specific guide catheter construction can be used to retain the connecting section or a portion thereof of the suction extension within the guide catheter lumen. Specifically, the tubular portion of the guide catheter can have a tubular segment at the distal end of the guide catheter having a slightly smaller inner diameter. Since the clearance can be made small between the connecting section and the guide catheter, a modest step down of the guide catheter diameter can limit the further distal movement of the suction extension. The construction of the guide catheter with the smaller diameter distal tubular element can be incorporated into the catheter assembly process to provide a stable construction.

In comparison with a suction catheter delivered through the guide catheter in which the suction flow is confined to the suction catheter, a significant length of the suction catheter is replaced with a control element in the suction catheter systems herein. This replacement of a significant length of a suction catheter with a control element results in a device that can have less friction when the tip of the suction catheter is advanced in the patient's vasculature since a control wire or other control element can offers less resistance for its movement. The tip of the suction extension can be given a curved tip to facilitate tracking of the device over a guidewire. With the designs described herein, a suction extension for aspiration with a curved tip for tracking the tip over a guidewire can be effectively guided too difficult to reach locations with the use of a control wire or other control element moving the slide portion at or near the distal end of the suction extension, and the design provides for good suction ability without sacrificing the ability to reach difficult to reach vessels, such as within cerebral vessels. While the suction extension is moved, the guide catheter portion of the suction lumen can remain in place When suction is applied at or near the proximal end of the guide catheter with a suitable negative pressure device, fluid is sucked into a distal opening at the end of the suction extension. It has been found that strong suction can be transmitted through to the suction extension. A suction lumen extends from a negative pressure device, generally attached at a fitting associated with a proximal section, at or near the proximal end of the suction system through the guide catheter lumen to the suction extension and through the connecting section of the suction extension and the tubular extension of the suction extension to a distal opening. Suitable negative pressure devices include, for example, syringes, pumps or the like. The guide catheter can provide a large lumen as a significant section of the overall suction lumen. The effective suction lumen then can appear to have a large proximal section contributed by the guide catheter and a tapered distal section contributed by the suction extension, which can have one or more tapered segments.

The tubular extension of the suction extension has a lumen with a reduced diameter relative to the guide catheter lumen and good flexibility to provide for placement of its distal end into smaller vessels. The lumen of the tubular extension though is maintained at a sufficiently large diameter that provides for delivery of additional therapeutic devices through the lumen to the treatment location. The outer diameter at the tip of the suction extension generally is (diameter in mm=(Fr value)/3, Fr represents the French catheter scale) at least about 1.5Fr less than the outer diameter of the distal section of the guide catheter. The smaller diameter of the tubular extension can provide access to desirable vessels, such as cerebral vessels.

It was previously discovered that good suction properties could be obtained with a suction catheter with a stepped down diameter in a distal section. Thus, for example, the majority of the length of the suction catheter can be 6Fr outer diameter while a distal section may be 5Fr outer diameter, which roughly corresponding decreases in the inner diameters. Such a catheter can provide access into vessels suitable for a 5Fr catheter, but can provide significantly better suction than a suction catheter with a 5Fr catheter body along its entire length. Commercial stepped down suction catheters, such as Mi-Axus™ catheters (MIVI Neuroscience, Inc.) and ACE™ 64 catheters (Penumbra, Inc.) are finding good clinical results. The step down suction catheters and their use for thrombectomy procedures in cerebral arteries are described in U.S. Pat. No. 9,532,792 B2 to Galdonik et al. (hereinafter the '792 patent), entitled "Aspiration Catheters for Thrombus Removal," incorporated herein by reference. While these catheters achieve better suction than catheters with constant diameters corresponding with the distal diameters, the present suction catheter systems with a sliding suction extension are found to provide better suction suggesting that the diameter over the majority of the suction lumen length contributes to a large extent to the suction provided at the distal opening of the suction lumen.

An initial part of a procedure using the devices described herein generally involves accessing the treatment location within the vasculature. Guidewires have been designed to facilitate access to difficult to reach locations. The term guidewire is used herein to refer broadly to wire structures that may or may not have internal structure are referred to as guidewires whether or not they are formed from a solid or woven metal, such as corewire-overtube integrated structures, coils or the like which may not have a closed inner lumen over at least a portion of the devices length.

In particular, with the devices described herein procedures can be performed to provide re-profusion in vessels that are blocked completely or partially with clots. Clots in cerebral arteries can cause strokes with corresponding serious consequences, and time generally is of the essence of treating these conditions. The suction extension with the guide catheter can be used to provide aspiration that can be useful to remove clots or fragments thereof. Thus, the suction extension combined with the guide catheter and negative pressure device can be used as stand-alone devices for thrombectomy procedures. However, the suction extension with aspiration can be effectively used as part of a treatment system comprising, for example, also a fiber based filter and/or other components to facilitate removal of a clot or portions thereof. The delivery catheter with the expandable tip is designed to facilitate access, so it is useful as a tool for the practice of various other procedures.

In some embodiments of the procedure, a guidewire can be placed at or near an occlusion and a guide catheter with a positionable suction extension can be placed in the vasculature upstream from the occlusion with the guidewire extending through the interior of the suction extension. If the suction catheter system is to be used alone, then the suction extension can be advanced using a control wire over the guidewire to a suitable position near the clot. Then, with or without removing the guidewire, suction can be initiated to suck the clot or a portion thereof into the distal opening or against the tip of the suction extension. Suction may or may not be continued as the suction extension and/or guide catheter are removed from the patient.

While suction with the suction extension can be effective as the only device for clot removal, additional treatment systems can combine other devices for use with the suction catheter system. In particular, a filter device can be used to provide both embolic protection as well as a tool to facilitate removal of the clot or portions thereof, which may involve direct engagement of the clot with the filter device. Fiber based filters/embolic protection systems have been developed that can be effectively used in the narrow vessels of interest. In particular, fiber-based filter systems with an appropriate actuation system can be used for delivery in a low profile configuration past an occlusion and deployed to provide protection from any clot fragments that may be released during the removal process.

During the removal process of the suction catheter system and potentially other components of the treatment system from the patient, aspiration generally is continued until risk for embolization of thrombus is sufficiently lowered. The suction extension may have thrombus within the lumen and/or trapped at the tip. The proximal end of a tubular section of the suction extension generally is open such that if the proximal end of the tubular extension is removed through a hemostatic valve, the suction lumen of the tubular extension can be exposed to the ambient environment. Since exposure of the lumen of the tubular extension still within the patient can be undesirable, fittings have been devised as described herein that allow parking of the tubular extension external to the guide catheter while still within isolated sections of the system external to the patient. Aspiration can be continued while the tubular extension is removed from the patient and parked in isolation from the ambient but external to the guide catheter. Generally, a control structure of the suction extension extending proximally can pass through a hemostatic valve with the valve closing around the control structure with an appropriate seal. With the tubular extension safely parked external to the guide catheter, the procedure can be completed, which generally involves termination of suction and confirmation that the blockage is resolved. At the end of the procedure, the guide catheter can be safely removed from the patient.

Throughout the part of the procedure in which aspiration is applied, the pressure in the proximal fittings can be monitored. If the pressure in the proximal fittings remains within an expected range, the physician performing the procedure can proceed based on that knowledge. If the pressure increases, the physician can take appropriate actions, such as removing the suction extension from the patient, generally without the delivery of fluid through the tubular extension.

The devices and corresponding processes described herein provide improved functionality for performing therapeutic procedures for the removal of clots from vessels. As noted herein, the devices can be used in various combinations within medical systems for percutaneous procedures. Improved procedures provide additional safety measures while providing practical steps for performance by the medical professional handling the devices.

Suction System With Sliding Suction Extension

Suction Systems are described that take advantage of good suction available with a suction catheter lumen having a larger proximal suction and a narrower diameter suction extension that uses the guide catheter lumen as a proximal suction lumen. A laterally slidable suction extension extends from a proximal section located within the guide lumen, and the suction extension can have a smaller diameter to provide access to narrow vessels while providing for delivery of other treatment structures and/or embolic protection structures as well as for a desirable level of suction for the removal of debris from the vessel. A control wire or other control structure can be attached to the suction extension to control sliding for providing selective lateral placement of the suction extension relative to a fixed guide catheter and a target treatment location. In some embodiments, the suction extension comprises a connecting section that interfaces with the guide catheter lumen with a non-cylindrical cross section to provide for contact at two parts along the circumference. This non-cylindrical interface can block flow between the exterior of the proximal portion of the suction extension and proximal locations in the interior of the guide catheter while allowing relatively easy sliding of the suction extension relative to the guide catheter. A specific guide catheter design can incorporate various tubular elements along its shaft to provide for desired flexibility and a narrower diameter distal tubular element can be used to retain the proximal section of the suction extension within the guide catheter lumen.

Referring to FIG. 1, suction system 100 comprises a suction adapted guide catheter 102 and a suction extension 104. The suction adapted guide catheter 102 comprises proximal section 106 and tubular shaft 108. Proximal section 106 generally is suitable for use also as a handle and generally can comprise a proximal fitting 120, a suction port 122 and an optional control wire port 124, as well as possibly other additional ports and/or fittings to provide desired functionality and access, in which all such ports and fittings can be arranged in a branch configuration or other suitable configuration. In general, proximal fitting 120 can comprise a suitable hemostatic valve, luer fitting or the like to provide for entry of a guidewire and/or structures delivered over the guidewire into the guide catheter lumen, such as alternative treatment structures and/or embolic protection devices.

In improved embodiments described herein, proximal fittings 120 can comprise a segment in which a tubular extension of suction extension 104 can be placed without extending into tubular shaft 108 of guide catheter 102 or through a hemostatic valve into the ambient environment. While desired features of fittings at the proximal end of the suction system 100 can be integral with proximal fitting 120, design flexibility can be achieved through embodiments of proximal fitting 120 comprising a connector, such as a Tuohy-Borst connector, and connection of fittings providing other desired features, such as a Y-branch, hemostatic valve, an extended tubular fitting to store the tubular extension of suction extension, etc. as fitting components that are attached for use to proximal fitting 120. Suitable fittings for incorporation with proximal fittings 120 are described in detail below in the treatment system section with an understanding that this disclosure below can be considered as integral portions of proximal fitting 120 rather than separate components.

For use with suction system 100, suitable embolic protection devices can be mounted on a guidewire, and/or other treatment structures can be used. Suitable treatment structures are described further below and can include, for example, fiber-based filters, stents, stent retrievers, atherectomy devices or the like. As shown in FIG. 1, a negative pressure device 126 is shown connected with suction port 122, and suitable negative pressure devices include, for example, syringes, pumps, such as peristaltic pumps, piston pumps or other suitable pumps, aspirator/venturi, or the like. Suitable pumps are available from Allied Healthcare Products, Inc., such as a Gomco™ brand pump, or a DRE DM-660™ pump.

In general, tubular shaft 108 can have an approximately constant diameter along its length, or some guide catheters can have sections with different diameters, generally with a smaller diameter section distal to a larger diameter section. In some embodiments described herein, a significant of the length of the tubular shaft has a constant diameter to make desired contact with a connecting section of the suction extension, which can be called an engagement section of the tubular shaft designed to engage the suction extension in a configuration suitable for the delivery of suction to a patient. Portions of the tubular shaft proximal to the engagement section can have a larger inner diameter and generally larger outer diameter relative to the engagement section. While a conventional guide catheter can be used in some embodiments for the suction catheter system, a specific design is described in detail below. A distal tubular portion of the tubular shaft can have a slightly narrower inner diameter to retain a portion of suction extension 104 within tubular shaft 108. Tubular shaft 108 can have one or more radiopaque marker bands to facilitate positioning of the tubular shaft within the patient as well as positioning the connecting section of the suction extension within the guide catheter lumen, and FIG. 1 shows a marker band 128 near the distal end of tubular shaft 108, although alternative positions can be used as desired. As described below, tubular shaft 108 can have coatings on the inner surface and/or the outer surface or portions thereof.

Suction extension 104 generally comprises a connecting section 140, tubular extension 142, and control structure 148, such as a control wire. All or a part of connecting section 140 can be configured to remain within the lumen of guide catheter 102. As shown in FIG. 1, connecting section 140 can comprise a radiopaque marker band 152, although connecting section may not have a marker band in some embodiments and in other embodiments can comprise a plurality of marker bands, and tubular extension 142 is shown with radiopaque marker band 154 near the distal tip of tubular extension 142, although again tubular extension 142 can comprise a plurality of radiopaque marker bands if desired. Control structure 148 can be a control wire or the like that connects with proximal portion 140 and in the assembled device extends exterior to the catheter, such as exiting through control wire port 124 or proximal fitting 120. Control structure 148 can be used to control positioning of connecting section 140 within the lumen of shaft 106. Control structure 148 can comprise a control tool 156, such as a handle, slide or other the like that can anchor a control wire or other connecting element to facilitate movement of the control wire. In some embodiments, alternative structures such as a plurality of wires or cylindrical wire assembly can connect the proximal portion to the proximal end of the suction catheter system to provide a desired level of control with respect to positioning the proximal section.

As noted above, the connecting section of suction extension engages the inner lumen of the guide catheter with an appropriate interface to reduce or eliminate flow of blood between the connecting section of the suction extension while allowing for the user to translate the suction extension relative to the guide catheter to position the tip of the tubular extension. A desirable design with a connecting section of the suction extension having a non-circular cross section has been found to particularly meet these criteria. With material selection as described herein, a very small average clearance can also be used between the connecting section of the suction extension and the interior of the guide catheter. When assembled, the inner lumen of the guide catheter can contact the connecting section of the suction extension at two locations around the circumference, which can provide partial rounding the cross section of the connecting section. This two location contact configuration provides desirable confinement of the flow while allowing for sliding of the suction extension by the user with appropriate ease.

The non-circular cross section of the connecting section (or a portion thereof) of the suction extension generally can be roughly oval in shape. While not intending to be limited by this term, in some embodiments, the cross section can have one axis of symmetry resembling the cross section of a conventional egg. As described below, the oval shape can be generated through the attachment of a wire control structure to the proximal section, although other structural features can be used to introduce the oval shape, such as with approximately one axis of symmetry or two axes of symmetry, although the oval can be asymmetric. Generally, the oval cross section can be partially characterized by a major axis, e.g., the longer dimension along an axis of symmetry, and a minor axis, e.g., the longest line segment connecting the circumference perpendicular to the major axis. While the specification of the major axis and the minor axis does not fully specify the oval since the specific shape is not specified, the major and minor axes can provide significant information regarding the dimensions and relative shape of the oval, especially since the shapes are generally not far out of a circular shape. Also, an average clearance can be defined using the largest value of the circumference (C) of the oval cross section and converting to an equivalent circle to define an approximate average diameter ($D_a = C/\pi$).

An embodiment of a guide catheter is shown in FIGS. 2-4. Referring to FIG. 2, guide catheter 160 comprises a connector fitted hub 162 with a portion of a Tuohy-Borst connector, luer connector or the like, shaft 164 and strain relief support 166. In this embodiment, the proximal end of shaft 164 passes through strain relief support 166 to connector fitted hub 162, and the components can be secured together with adhesive. Also, female connector 168 is located at the proximal end of connector fitted hub 162 for connection to a male connector fitting on a proximal fitting, such as a branched connector, which may have a rotating hemostatic valve with one or more branches.

A sectional view of a portion of shaft 164 near the proximal end is shown in FIG. 3. Referring to the embodiment of FIG. 3, shaft 164 comprises a polymer tube 180 with an embedded stainless steel wire braid 182 and a lubricious liner 184, e.g., polytetrafluoroethylene (PTFE) or other fluoropolymer. FIG. 4 shows the distal end of shaft 164. As shown in FIG. 4, a radiopaque marker band 186 is embedded in the polymer tubing near the distal end of shaft 164. Also, a distal section 188 of tubing is placed at the distal end of shaft 164 with a slightly reduced inner diameter, as explained further below. As shown in FIGS. 3 and 4, the metal braid ends adjacent marker band 186 (or overlaps with the marker band and terminates after), and distal section 188 is free of metal braiding in this embodiment. As described further below, the composition of the polymer tubing included in the shaft can vary along the length of shaft 164, for example, to increase flexibility of the shaft toward the distal end of the shaft. In some embodiments, different adjacent sections of polymer tubing can be heat bonded together and further supported with an overarching metal braiding and/or coil reinforcing the majority of the shaft. In some embodiments, the majority of the shaft 164 can have a constant inner diameter, except for distal section 188, to provide for the application of suction through the suction extension positioned at any location within the guide catheter proximal to distal section 188. But in alternative embodiments, a proximal section of shaft 164 can have a larger diameter if desired since the proximal section of the guide catheter may not be used for positioning the connecting section of the suction extension for the application of suction. Appropriate markers on the control wire can be used to ensure that the suction extension is positioned properly for the application of suction.

A lubricious coating, for example, a hydrophilic coating, can be placed on the outer surface of shaft 164 or a portion thereof. Suitable hydrophilic coatings include, for example, polyvinyl alcohol, heparin based coatings, or the like. Hydrohylic coating solutions are commercially available, such as LUBRICENT® (Harland Medical Systems, MN, USA) or SERENE™ (Surmodics, Inc, MN, USA). Further description of the materials and manufacturing process are provided below.

The guide catheter can have an outer diameter (D) from about 5.5 Fr (1.667 mm diameter) to about 10 Fr (3.333 mm diameter), in further embodiments from about 6 Fr (1.833 mm diameter) to about 9 Fr (3 mm diameter), and in some embodiments from about 6.25 Fr (2 mm diameter) to about 8.5Fr (2.833 mm diameter). The guide catheter measurement are generally referenced to the outer diameter, and the inner diameter is less than the outer diameter by twice the wall thickness. In general, the inner diameter of the main portion of shaft 164 ($d_1$) can range from about 0.8 mm to about 3.175 mm, in further embodiments from about 0.9 mm to about 2.85 mm and in additional embodiments from about 1.00 mm to about 2.7 mm. The reduction in inner diameter of distal section 188 ($d_2$) relative to the inner diameter of an engagement section of shaft 164 ($d_1$) can be from about 0.034 mm (0.00134 in) to about 0.25 mm (0.0098 in) and in further embodiments from about 0.05 mm (0.002 in) to about 0.20 mm (0.0079 in). The length of the guide catheter shaft (L) can be from about 30 cm to about 150 cm, in further embodiments from about 35 cm to about 130 cm and in additional embodiments from about 40 cm to about 120 cm, and is generally selected to be suitable for the corresponding procedure. In some embodiments, distal section 188 can have a length (Ld) from about 1 mm to about 50 mm, in further embodiments from about 1.5 mm to about 25 mm, and in other embodiments from about 2 mm to about 20 mm. A person of ordinary skill in the art will recognize that additional ranges of dimensions within the explicit ranges above are contemplated and are within the present disclosure.

For use of the guide catheter of FIG. 2 to form analogous proximal fittings of FIG. 1, a Y-branch hemostatic valve connector 190 can be used, such as the embodiment shown in FIG. 5. Y-branch hemostatic valve connector 190 comprises a male connector 192, a Y-branch frame 194 with branching flow channels, rotating hemostatic valve 196, connector 198, tubing 200 connected to Y-branch frame 194 at connector 198, and suction device 202 connected to tubing 200. Male connector element 192 can be attached to female connector element 168 of FIG. 2. As schematically shown in FIG. 5, a control wire 204 and a guidewire 206 are both shown exiting hemostatic valve 196, and guidewire 206 can be used to guide therapeutic devices through a guide catheter through the hemostatic valve. Various branched hemostatic valve connectors are available from commercial suppliers, such as Merit Medical, UT, USA. More generally, a range of fittings can be attached to connector fitted hub 162 of guide catheter 160, and improved embodiments of fittings with a portion for placement of the tubular extension of the suction extension are described in more detail under the treatment systems section below.

An embodiment of a suction extension is shown in FIGS. 6-12. Referring to FIG. 6, suction extension 230 comprises a control wire 232, connecting section 234 and tubular extension 236. Connecting section 234 connects with control wire 232, which extends in a proximal direction from the connecting section, and tubular extension 236, which extends in a distal direction from the connecting section. In general, control wire 232 can be a solid wire, coil or the like that provides for transmission of pulling and pushing forces to connecting section 234, which correspondingly can move with the tubular extension 236 relative to a guide catheter in the assembled suction catheter system. Control wire 232 can have any reasonable cross sectional shape, which can be different at different locations along the length of the control wire. Also, the control wire can be tapered to a smaller circumference toward the distal end of the control wire. Generally, control wire 232 is made of biocompatible metal, such as stainless steel, titanium or the like, although other materials that have appropriate balance of rigidity and flexibility can be used in principle. In some embodiments, the control wire is a round metal wire with an average diameter along its length from about 0.010 inches (0.254 mm) to about 0.040 inches (1.01 mm) and in further embodiments from about 0.0125 inches (0.32 mm) to about 0.030 inches (0.76 mm). The length of control wire 232 is generally somewhat longer than the guide catheter so that the guide wire extends from the proximal end of the guide catheter, such as 5 cm or more longer than the guide catheter. A person or ordinary skill in the art will recognize that additional ranges within the explicit dimensional ranges above are contemplated and are within the present disclosure.

Connecting section 234 generally is distinguishable by a larger outer diameter than tubular extension 236, and tubular extension 236 extends from the connecting section 234 in a distal direction. In the embodiment of FIGS. 6-12, tubular extension 236 has an approximately constant outer and inner diameter, and a further embodiment is described below with a step down diameter along the tubular extension. Referring to a sectional view in FIG. 10, tubular extension comprises a polymer tube 240, a metal coil reinforcement 242 and a radiopaque marker band 244. Metal coil reinforcement 242 can comprise a flat metal wire, which can extend in some embodiments from roughly radiopaque marker band 244 to a radiopaque marker band in connecting section 234, described further below, although the metal coil reinforcement can extend over the marker bands. Polymer tube 240 can remain the same along the length of tubular extension 236, or the polymer can be changed as different positions along tubular extension 236, for example, getting more flexible in a distal direction. Different sections of polymer can be heat bonded during construction, and metal coil reinforcement 242 as well as optionally a polymer overlayer can further stabilize connected sections of polymer tubing. A tip 246 of tubular extension 236 distal to radiopaque marker band 244 can comprise polymer tubing 240 free of metal reinforcement. A low friction liner 248, such as PTFE or other fluoropolymer, can extend along the length of tubular extension 236 and/or connecting section 234, or portions thereof.

The relationship of connecting section 234 with control wire 232 and tubular extension 236 are shown in FIGS. 6-8. Sectional views of portions of connecting section 234 are shown in FIGS. 9, 11 and 12 and show certain details of the structure. Connecting section 234 can comprise polymer tubing 260 and radiopaque marker band 262. Polymer tubing 260 has a proximal opening 264 that can be angled relative to a longitudinal axis of the polymer tubing to facilitate delivery of devices through the suction extension, although a right angle can be used if desired. The angle α is marked on FIG. 8 and can range from 25 degrees to about 85 degrees, in further embodiments from about 30 degrees to about 80 degrees, and in additional embodiments from about 33 degrees to about 75 degrees. A person of ordinary skill in the art will recognize that additional ranges of angles within the ranges above are contemplated and are in the present disclosure.

The interface of control wire 232 with connecting section 234 can serve the purpose of both securing the components together as well as helping to form the shape of connecting section 234, which can be selected to provide a desired interface with the interior of the guide catheter lumen. Specifically, the connection of the control wire with the connecting section can facilitate the formation of the oval cross section of the connecting section. In alternative embodiments, control wire 232 can terminate with a flat wire coil that is embedded into a polymer tube to substantially maintain the shape of the connecting section, as described in the '938 application and below. In additional or alternative embodiments, an oval shape of the connecting section can be introduced through the molding or other shaping of the polymer which may or may not be combined with a bump due to an embedded control wire. Suitable dimensions of the oval cross section and the processing to form the connecting section are described further below. Low friction liner 248 can extend through the inner lumen of connecting section 234, as shown in FIGS. 9 and 11, or in some embodiments a separate low friction liner can be included in connecting section 234 if desired.

Figure 13:
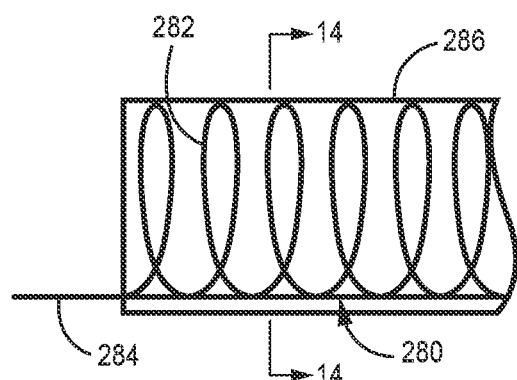
FIG. 13 is a fragmentary side view of an alternative embodiment of a suction extension with the expanded insert showing the attachment of a control wire to the proximal portion using a coiled end portion of the control wire.
Figure 14:
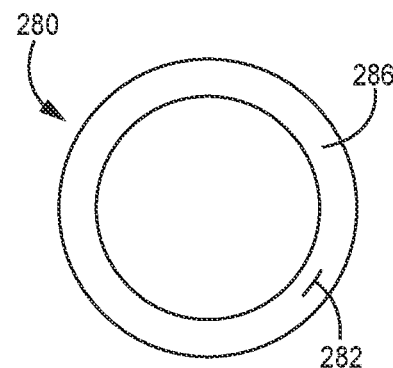
FIG. 14 is a sectional view taken along line 14-14 of FIG. 13.
Figure 21:
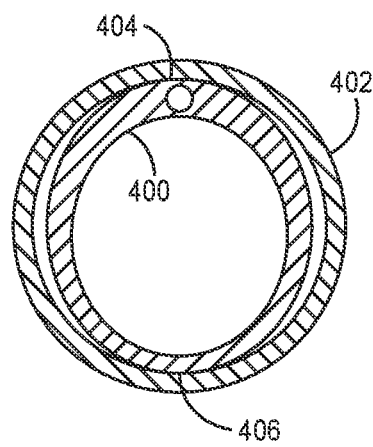
FIG. 21 is a sectional end view of a connecting section of a suction extension interfacing with engagement section of a guide catheter with a non-circular cross section.
Figure 22:
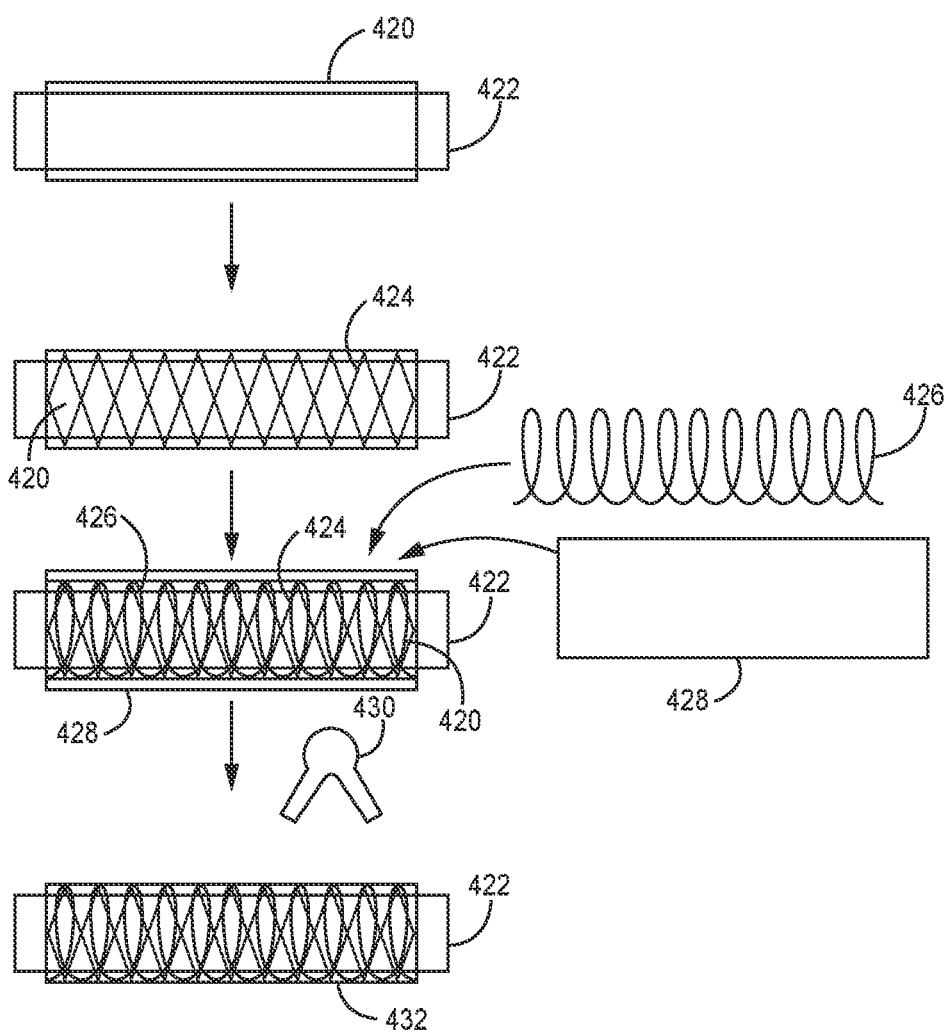
FIG. 22 is a series of side views depicting the construction of a catheter structure on a mandrel in which one or more steps are performed including application of a wire braiding, placement of a metal coil, application of a polymer over sheet and heating the polymer to embed the metal structures within the polymer.

Referring to FIGS. 8, 11 and 12, the distal end of control wire 232 is embedded in polymer associated with polymer tubing 260. Supplementing the polymer wall to secure control wire 232 alters the cross sectional shape that results in a major axis ($L_M$) greater than the minor axis ($L_m$), as can be seen clearly in FIG. 12. As noted above, the non-circular cross section is advantageous for the interface of the suction extension with the guide catheter. The cross section of an alternative embodiment of a connecting section 280 with a non-circular shape is shown in FIGS. 13 and 14. In this embodiment, a flattened metal coil 282 at the end of a control wire 284 is embedded in a polymer tube 286 with a noncircular cross section. The non-circular cross section is formed in this embodiment through forming the polymer with a thicker wall along one edge of the circumference, as can be seen in the sectional view of FIG. 14. A corresponding circular embodiment is shown in FIGS. 21 and 22 of the '938 application. The connecting section may or may not have an approximately constant outer diameter over its length, and the outer diameter may taper, e.g. a gradual taper, step-wise taper or combination thereof, over at least a portion of its length to roughly the outer diameter of the adjacent section of the tubular extension.

An alternative embodiment of a suction extension is shown in FIGS. 15 and 16. Suction extension 300 comprises control wire 302, connecting section 304 and tubular extension 306. Control wire 302 and connecting section 304 can be analogous to control wire 232 and connecting section 234, respectively, for the embodiment of FIGS. 6-12. Referring to FIG. 16, the distal end of control wire 302 is embedded in polymer within connecting section 304 forming a distension 308 along a surface of connecting section 304. A proximal opening 310 into the lumen of connecting section 304 forms an angle α with respect to the axis of connecting section 304. Connecting section 304 comprises a radiopaque marker band 312. The body of connecting section 304 is a polymer tube 314. Low friction liner 316, such as PTFE or other fluoropolymer, can extend along the lumen of connecting section 304 and/or tubular extension 306 or selected fractions thereof. Metal reinforcement, such as a flat metal wire coil, can reinforce polymer tube 314 or a fraction thereof. As shown in FIG. 16, flat metal wire coil 318 is embedded through the polymer tube 314 distal to radiopaque marker band 312 and extending to tubular extension 306. Furthermore, the asymmetric cross section shown in FIGS. 12 and 14 as well as the control wire attachment approaches of FIGS. 11 and 13 can apply also to the embodiment of FIGS. 15 and 16.

Figure 17:
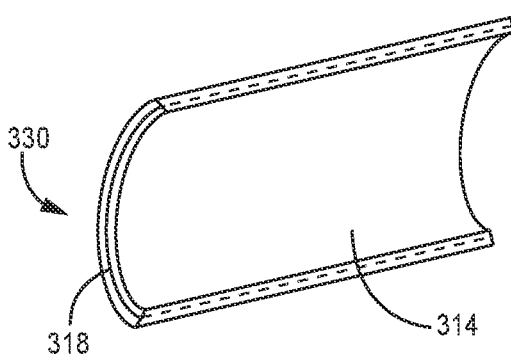
FIG. 17 is a cut-away portion of a catheter wall showing some features of its construction.

Referring to FIGS. 15 and 16, tubular extension 306 comprises a first tubular section 330, taper section 332 and second tubular section 334 having a smaller diameter than first tubular section 330. Taper section 332 tapers between the diameter of first tubular section 330 and the diameter of the second tubular section 334. Second tubular section 334 comprises a radiopaque marker band 336. Flat metal wire coil 318 extends from radiopaque marker band 336 to radiopaque marker band 312 within connecting section 304, embedded within a polymer tube. The end of second tubular section 334 distal to radiopaque marker band 336 can be free of metal reinforcement. As noted above, a low friction liner 316 can extend along lumen wall for the length of tubular extension 306 or a selected fraction thereof. The body of the first tubular section 330, taper section 332 and second tubular section 334 generally comprises a thermoplastic polymer tube. Sections of polymer tube can be heat bonded together and further supported by the embedded flat metal wire coil 318, optionally with heat shrink polymer film or the like covering the metal reinforcement. A fragmentary sectional view of first tubular section 330 is shown in FIG. 17 with flat metal wire coil 318 shown embedded in polymer tube 338, and cross sectional views of taper section 332 and second tubular section 334 would show similar construction. The composition of the polymer tube can vary along the length as desired to select a particular flexibility, generally more flexible toward the distal end of the device, and the polymer composition can be varied for the different section 330, 332, 334 and/or within the sections.

As shown in FIGS. 15 and 16, taper section 332 provides an approximately linear transition of diameters from the wider diameter of first tubular section 330 to the narrower diameter of second tubular section 334. In alternative embodiments, a taper section can have nonlinear changes in diameter if desired, but the change is generally monotonic. The taper section can be formed through an extrusion process or through conforming of a thermoplastic polymer to a mandrel shape or other suitable process approach known in the art.

A significant aspect of the suction extension is the narrower diameter suction tip relative to the guide catheter, and the step down diameter of the second tubular section of the embodiment of FIGS. 15 and 16 allow for further reach into narrow neurovascular vessels. The effective suction lumen then extends through the guide catheter into the connecting section of the suction extension and then into the tubular extension, which can have further step downs in diameter. The inner diameter of the connecting section may or may not be the same as the inner diameter of the first tubular section. The narrow diameter of the tubular extension provides for reach into small circuitous blood vessels and the use of the larger diameter proximal suction lumen improves the suction performance significantly without detracting from the ability to reach appropriate locations.

To further provide for suction strength, the tubular extension itself can have different sections with stepped down diameters, such as shown in the embodiment of FIGS. 15 and 16. In general, the arteries progressively decrease in diameter so a section with a somewhat larger diameter may be desirable consistent with the reach of the suction tip into a selected narrow vessel. With respect to first tubular section, this section generally has an approximately constant diameter (generally inner diameter or outer diameter with an assumption of approximately constant wall thickness) that is generally from about 0.95D to about [d+0.1(D-d)], in further embodiments from about 0.925D to about [d+0.25(D-d)], and in some embodiments from about 0.9D to about [d+0.35(D-d)], where d is the diameter of second tubular section and D is the average diameter of the connecting section. The length of first tubular section can be from about 10% to about 90%, in further embodiments from about 20% to about 80% and in additional embodiments form about 30% to about 70% of the total length of tubular extension, e.g., the total length of first tubular section, second tubular section, and the optional transition section or just a single tubular section for corresponding embodiments ($L_T$ in FIG. 6). The connecting section can have a length ($L_C$ in FIG. 6) from about 4 mm to about 8 cm and in further embodiments from about 5 mm to about 6 cm. A person of ordinary skill in the art will recognize that additional ranges of dimensions and relative dimensions within the explicit ranges above are contemplated and are within the present disclosure. While FIGS. 15 and 16 show a tubular extension with one step down in diameter to a second tubular section, in other embodiments there can be additional constant diameter tubular sections further stepping down the diameter, which further divide the length of the entire tubular extension specified above. For example, there can be a further intermediate tubular section, two further intermediate tubular sections or more than two further intermediate tubular sections.

The tubular extension or distal tubular section of the tubular extension for embodiments with a plurality of tubular sections with different inner diameters can have an inner diameter from about 20 percent to about 90 percent of the inner diameter of the engagement section of the guide catheter, and in further embodiments from about 30 percent to about 85 percent and in additional embodiments from about 35 percent to about 80 percent of the inner diameter of the engagement section of the tubular shaft. For example, the distal tip of the tubular extension can have an inner diameter in a range from about 0.5 mm to about 1.9 mm, in further embodiments from about 0.6 mm to about 1.8 mm, and in other embodiments from about 0.65 mm to about 1.75 mm. The tubular extension can have a length from about 3 cm to about 60 cm, in some embodiments from about 5 cm to about 55 cm and in further embodiments from about 8 cm to about 50 cm. A person of ordinary skill in the art will recognize that additional ranges of dimensions within the explicit ranges above are contemplated and are within the present disclosure.

Figure 18:
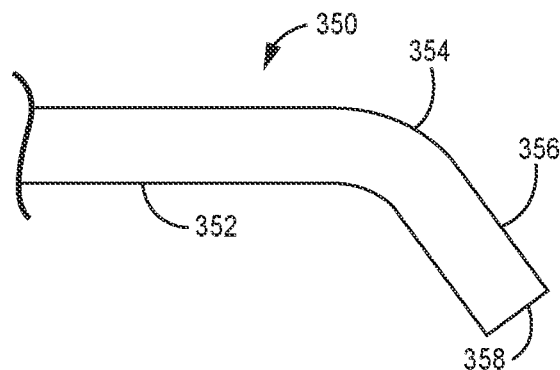
FIG. 18 is a fragmentary side view of a suction tip with a bend.
Figure 19:
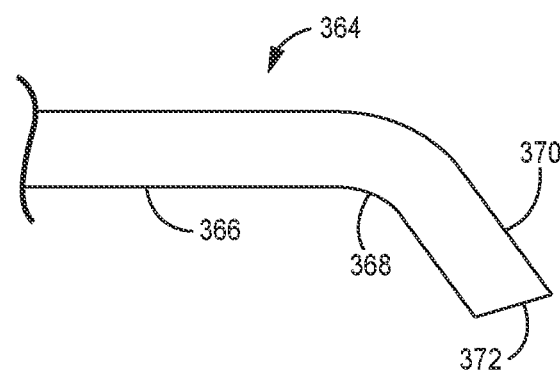
FIG. 19 is a fragmentary side view of a suction tip with a bend and an angled opening.

The distal tip of the tubular extension can be bent or curved in its natural unstressed configuration. It has been found generally that a bent tip catheter can facilitate tracking of the catheter over a guidewire without adversely altering the suction abilities. See, for example, U.S. Pat. No. 8,021,351 to Boldenow et al., entitled "Tracking Aspiration Catheter," incorporated herein by reference. Two general versions of a bent suction tip are shown in FIGS. 18 and 19. Referring to FIG. 18, suction tip 350 comprises a straight section 352, bend 354 and bent tip section 356 with a flat distal opening 358 approximately perpendicular to the axis of bent tip section 356. Referring to FIG. 19, suction tip 364 comprises a straight section 366, bend 368 and bent tip section 370 with an angled distal opening 372 at a non-perpendicular angle to the axis of bent tip section 370. Bent tip sections 356, 370 are generally cylindrical and can have approximately the same diameters as corresponding straight sections 352, 366. While two shapes of openings are shown in FIGS. 18 and 19, any reasonable shape of the opening generally can be used.

Figure 20:
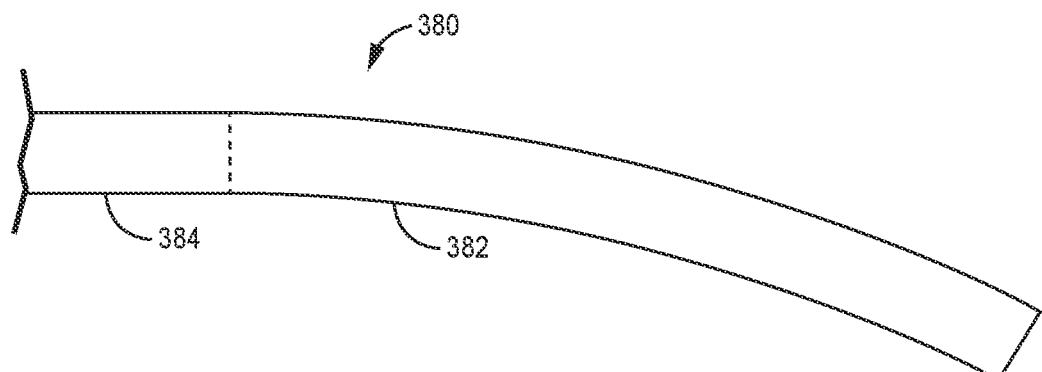
FIG. 20 is a fragmentary side view of a suction tip with a gentle curve.

A specific embodiment of a bent tip for a suction extension 380 is shown in FIG. 20. In this embodiment, the distal tip 382 is curved with no straight section at the distal end in this embodiment, although alternative embodiments can have short straight segment at the distal end. Distal tip 382 extends from a straight section 384 of suction extension 380. The arc of the curve is approximately circular, but other gentle arcs can be used, in which case the radius of curvature can be an average over the arc.

In this embodiment, the curvature of the tip is gradual so that the distal tip may not have a straight section. An angle γ can be defined based on the point of initial curvature and the natural position of the tip taken at the middle of the distal opening. In some embodiments, angle γ can be from about 5 degrees to about 21 degrees and in further embodiment from about 7 degrees to about 20 degrees. To achieve the gentle curvature, the radius of curvature generally is relatively large, and in some embodiments, the radius of curvature can be from about 21 mm to about 100 mm and in further embodiments from about 25 mm to about 75 mm. In some embodiments, a straight portion of the tip after the curve can have a length no more than about 1 cm, and in other embodiments from about 0.1 mm to about 6 mm and in further embodiments from about 0.5 mm to about 4 mm. In alternative embodiments, the curve consists of a gradual arc with no significant straight section distal to it, such that the curve or bend is specified by the angle and radius of curvature. A person of ordinary skill in the art will recognize that additional ranges of angles, radii and lengths within the explicit ranges above are contemplated and are within the present disclosure.

As noted above, the connecting section of the suction extension can have a non-circular, oval cross section, which can interface then with the inner surface in the lumen of the guide catheter to contact the inner surface at two locations along the circumference. The interface between the connecting section of the suction extension and the engagement section of the guide catheter reduces or eliminates any flow between surfaces so that essentially all of the suction flow passes through the lumen of the suction extension. At the same time, the suction extension can be positioned longitudinally within the engagement section to position the suction extension by a user through sliding the control structure. These various conditions can be balanced effectively to provide the desired functionality.

Referring to FIG. 21, a sectional view is shown of a connecting section 400 of a suction extension within an engagement portion 402 of a guide catheter. The non-cylindrical nature of the cross section of connecting section 400 is readily visible. Due to the interface between the elements, the oval shape of connecting section 400 can be distorted relative to its shape separated from the guide catheter, especially if the undistorted length of the major axis of the connecting section 400 is greater than the inner diameter of engagement portion 402. Connecting section 400 can contact the inner surface of the lumen of engagement section 402 at two contact locations 404, 406. The size of contact locations 404, 406 generally depends on the dimensions of the elements, the shape of connecting section 400 and the material properties. It is generally not necessary to precisely define the boundaries of the contact locations.

As noted above, the non-cylindrical connecting section can be characterized with the major axis, minor axis and an average diameter obtained from the circumference. Based on these parameters, it is possible to specify significant aspects of the interface between connecting section 400 and engagement portion 402 with a difference between the major axis and the minor axis, with a difference between the major axis of an unconstrained connecting section 400 and the inner diameter of engagement section 402, and with the difference between the inner diameter of engagement section 402 and the average diameter of connecting section 400. For example, the difference between the major axis and the minor axis can be from about 30 microns to about 160 microns and in further embodiments from about 50 microns to about 140 microns. In some embodiments, the tolerance measured as a difference between the diameter of the inner surface of engagement section 402 and the average diameter of the connecting section can be, for example, no more than about 4 thou (1 thou=1/1000 of an inch; 4 thou~102.6 microns), in further embodiments no more than about 3 thou (76.2 microns), in additional embodiments no more than about 1.75 thou (45 microns), in other embodiments from about 1 thou (25.4 microns) to about 1.75 thou (45 microns) and can be approximately zero within the measurement uncertainty. For embodiments in which the major axis of the connecting section separated from the guide catheter is larger than the guide catheter inner diameter, the difference between the major axis of unconstrained (i.e., separated from the guide catheter) connecting section 400 and the inner diameter of engagement section 402 can be from about 0 to about 250 microns, in further embodiments from about 15 microns to about 150 microns and in other embodiments from about 20 microns to about 100 microns. A person of ordinary skill in the art will recognize that additional ranges of dimensions differences within the explicit ranges above are contemplated and are within the present disclosure.

Catheter components can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, combinations thereof, or other suitable biocompatible polymers. Radio-opacity can be achieved with the addition of metal markers, such as platinum-iridium alloy, tantalum, tungsten, gold, platinum-tungsten alloy or mixtures thereof, such as wire or bands, or through radio-pacifiers, such as barium sulfate, bismuth trioxide, bismuth subcarbonate, powdered tungsten, powdered tantalum or the like, added to the polymer resin. Medical grade PEBAX is available commercially loaded with barium sulfate, as well as with ranges of Shore hardness values. Generally, different sections of aspiration catheter can be formed from different materials from other sections, and sections of aspiration catheter can comprise a plurality of materials at different locations and/or at a particular location. In addition, selected sections of the catheter can be formed with materials to introduce desired stiffness/flexibility for the particular section of the catheter. Similarly, fitting can be formed form a suitable material, such as one or more metals and/or one or more polymers.

In some embodiments, the guide catheter, suction extension or appropriate portions thereof comprises a thermoplastic polymer, such as the polymers listed above, with embedded metal elements, which reinforces the polymer. The wire can be braided, coiled or otherwise placed over a polymer tubing liner with some tension to keep the wire in place over the tubing liner. In some embodiments, a polymer jacket, such as a heat shrink polymer, can then be placed over the top and heated to shrink and fuse the cover over the structure, and/or the polymer tube can be softened with heat to allow incorporation of the metal reinforcements. Upon heating to a temperature over the softening temperature and/or heat shrink temperature of the polymer and subsequent cooling, the reinforcing metal becomes embedded within the polymer. In appropriate embodiments, a liner and a jacket can be the same or different materials. Suitable wire includes, for example, flat stainless steel wire or the like. Wire diameters can range from about 0.00025 inch (0.00635 mm) to about 0.004 inch (0.1 mm) and in further embodiments from about 0.0005 inch (0.013 mm) to about 0.003 inch (0.075 mm). For appropriate embodiments, braid picks per inch can be from about 20 to about 250 picks per inch and in further embodiments from about 50 to about 150 picks per inch. For appropriate embodiments, coils can be single or multiple filament coils having, for example, pitches from about 0.005 inch (0.13 mm) to about 0.1 inch (2.54 mm) and in further embodiments form about 0.01 inch (0.26 mm) to about 0.050 inch (1.27 mm). A person of ordinary skill in the art will recognize that additional ranges within the explicit ranges below are conceived and are within the present disclosure. The wire adds additional mechanical strength while maintaining appropriate amounts of flexibility. The wire can provide some radio-opacity although radiopaque bands generally would provide a darker and distinguishable image relative to the wire. However, the image of the wire can provide further visualization of the catheter during the procedure.

To decrease the chance of accidental removal of the radiopaque band from the catheter and to decrease the chance of the radiopaque band catching onto other objects within the vessel, a metal reinforcing wire can be used to cover or enclose the radiopaque band with the metal wire subsequently being embedded within the polymer. In some embodiments, a polymer jacket can be placed over the metal wire, which is correspondingly covering the radiopaque band(s), and the heat bonding embeds the radiopaque marked band also. If desired, placement of the marker band under metal wire can prevent the band from being separated from the catheter in the event that the wall is kinked or collapsed. If collapse or kinking of the catheter wall occurs, the braid-wire over the surface of the band collapses down over the marker band to prevent it from separating from the structure.

Referring to FIG. 22, an example of a procedure for forming a section of reinforced catheter is shown. Polymer liner 420 is placed over mandrel 422. In the second sequential figure, metal braiding 424 has been placed over the polymer liner, and commercial braiding equipment can be used for this step. As shown in the third figure of the series, a metal coil 426 is placed over braided wire 424 and a polymer cover 428 is placed over the coil 426. A heat source 430 can be used to heat shrink polymer cover 428 to complete the reinforced catheter section 432, as shown in the fourth sequential figure of FIG. 22. Of course, in some embodiments, only a coil or only metal braiding can be used, and the procedure is correspondingly revised. Similarly and independently, a heat shrink cover may or may not be used, and again the procedure is correspondingly revised.

Treatment Systems

The suction system described herein can be used effectively to remove blood clots from the vasculature, including the vasculature of the brain to treat acute stroke conditions. In particular, the narrow tip catheter of the '792 patent have performed well in human clinical trials to restore blood flow in persons with an acute embolic stroke with good patient outcomes. The device described herein may be expected to provide even better suction while maintaining access capability into vessels challenging to navigate. Nevertheless, for some acute stoke conditions or other embolic events, it can be desirable to use the suction catheter systems described herein with other medical tools for performing the therapy. Furthermore, specific desirable embodiments of proximal fittings are described in this section that provide for improved procedures for use of the suction extension described herein. In particular, adaptations of the proximal fittings provide for removal of a tubular extension of the suction extension from the guide catheter without passage through a hemostatic valve. Also, the proximal fittings can be adapted with a pressure sensor that can provide valuable information about the status of the suction process. The availability of the pressure information can be used to improve aspects of the procedure to increase efficacy and to reduce potential risks to the patient.

Figure 23:
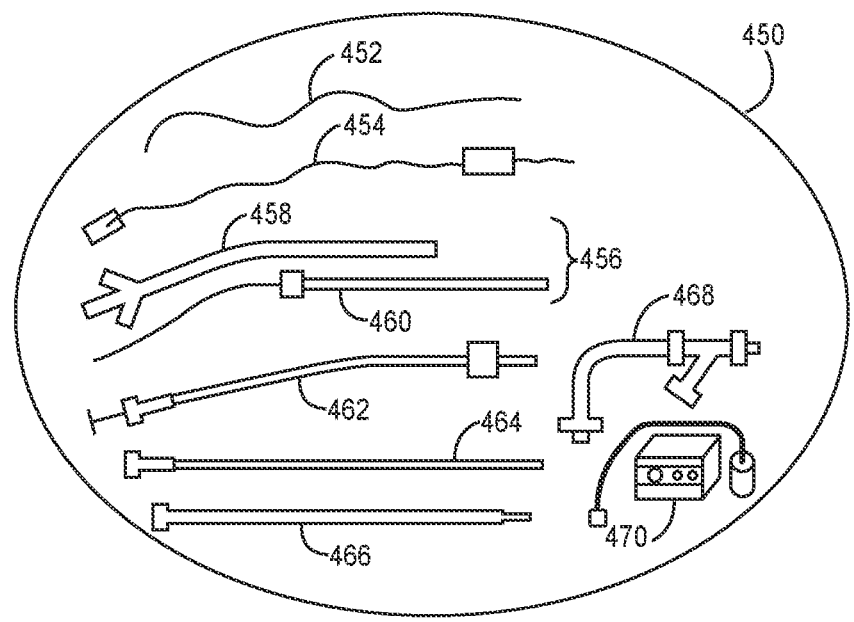
FIG. 23 is a schematic depiction of a collection of medical devices that can be used together or in selected sub-combinations for selected percutaneous procedures in bodily vessels including a suction system as described herein.

Referring to FIG. 23, a treatment system 450 is shown comprising a guidewire 452, embolic protection system 454, suction catheter system 456, shown with guide catheter 458 and suction extension 460 separated, a percutaneous medical device 462, a microcatheter 464, a delivery catheter 466, proximal fitting 468, and negative pressure device, e.g., pump or syringe, or the like, 470. Not all embodiments of medical systems may have all of these components, and some medical system embodiments may have multiple components of each type, such as multiple distinct percutaneous medical devices. Suitable structures for nozzle fitting 468 are discussed in the following section.

Guidewires suitable for use in tortuous bodily vessels are described in published U.S. patent application 2016/0199620 to Pokorney et al., entitled "Medical Guidewires for Tortuous Vessels," incorporated herein by reference. In some embodiments, embolic protection system 454 can comprise a guide structure to provide for delivery of the device as a guide wire, and for these systems a separate guidewire may or may not be used. Suction catheter systems 456 are described in detail herein, and the various embodiments described herein can be adapted for use with the medical systems as well as for use as stand-alone devices. If desired for particularly challenging device delivery, the medical system can include a delivery catheter 466, as described in the '938 application.

Embolic protection devices with small filter longitudinal extent and designed for suitable manipulations to facilitate delivery in vessels have been developed that are suitable for use in the medical systems described herein. See, for example, U.S. Pat. No. 7,879,062B2 to Galdonik et al., entitled "Fiber Based Embolic Protection Device," and U.S. Pat. No. 8,092,483B2 to Galdonik et al., entitled "Steerable Device Having a Corewire Within a Tube and Combination with a Medical Device," both of which are incorporated herein by reference. FiberNet® embolic protection devices based on the technology in these patents are commercially available from Medtronic Inc. Additional fiber-based filter devices particularly designed for delivery into tortuous vessels are described in U.S. Pat. No. 8,814,892B2 to Galdonik et al. (hereinafter the '892 patent), entitled "Embolectomy Devices and Method of Treatment of Acute Ischemic Stroke Condition," incorporated herein by reference. The '892 patent describes the use of the filter device as a clot engagement tool for use with an aspiration catheter. The '892 patent also envisions the use of supplementary structures to facilitate engagement of the clot. The use of supplementary structures are also contemplated in procedures described herein.

Microcatheters have been designed to allow for access to small blood vessels, such as cerebral blood vessels, and cerebral microcatheters are available commercially, e.g. Prowler Select™ (Cordis Neurovascular Inc.) and Spinnaker Elite™ (Boston Scientific Co.). Of course the term microcatheter can cover a range of devices, and the present discussion can focus on catheters useful for the procedures described herein. In some embodiments, microcatheters can comprise a distal section that is narrower than a proximal section. However, in further embodiments, a microcatheter can have an approximately constant diameter along its length to facilitate delivery of other devices over the microcatheter. A narrow distal diameter allows for the catheter to navigate the tortuous vessels of the brain. The distal section can be highly flexible enough to navigate the vessels, but resilient enough to resist kinking. A microcatheter comprises at least one lumen. The microcatheter can then be used to deliver other treatment devices, aspiration, therapeutic agents, or other means of treating a condition. While microcatheters can have a selected size, in some embodiments, the microcatheters can have a distal outer diameter from about 1.0Fr to about 3.5Fr and in further embodiments from about 1.5Fr to about 3Fr, and a length from about 30 cm to about 200 cm and in further embodiments from about 45 cm to about 150 cm. A person of ordinary skill in the art will recognize that additional size ranges within the explicit ranges above are contemplated and are within the present disclosure.

With respect to percutaneous medical devices 762, suitable devices include, for example, clot engagement devices, angioplasty balloons, stent delivery devices, atherectomy devices, such as stent retrievers, and the like. Desirable thrombus engagement devices are described in published U.S. patent application 2017/0056061 to Ogle et al., entitled "Thrombectomy Devices and Treatment of Acute Ischemic Stroke With Thrombus Engagement," incorporated herein by reference. Stents may be, for example, balloon extendable, self-extendable or extendable using any other reasonable mechanism. Also, balloon extendable stents can be crimped to the balloon for delivery to engage a clot in a blood vessel. Some balloon-stent structures are described further, for example, in U.S. Pat. No. 6,106,530, entitled "Stent Delivery Device;" U.S. Pat. No. 6,364,894, entitled "Method of Making an Angioplasty Balloon Catheter;" and U.S. Pat. No. 6,156,005, entitled "Ballon [sic] Catheter For Stent Implantation," each of which are incorporated herein by reference. Self-expanding stents are described further in U.S. Pat. No. 8,764,813 to Jantzen et al., entitled "Gradually Self-Expanding Stent" and U.S. Pat. No. 8,419,786 to Cottone, Jr. et al., entitled "Self-Expanding Stent," both of which are incorporated herein by reference. Stent retrievers are described, for example, in U.S. Pat. No. 8,795,305 to Martin et al., entitled "Retrieval systems and methods of use thereof," incorporated herein by reference.

Once the clot treatment process is completed, it has been found that it is advantageous to at least partially remove the tubular extension of the suction extension from the guide catheter before removing the guide catheter from the patient. If a portion of the tubular extension is removed through a hemostatic valve during this removal process, the isolation between the vasculature and the exterior of the patient can be lost since the proximal end of the tubular extension is not designed for closure. The loss of isolation between the exterior of the patient and the interior of the catheter system can result in an undesirable amount of bleeding as well as complicating the control of trapped thrombus associated with the nozzle The fitting designs described here are intended to address these issues through the inclusion of a tubular storage area distal to a hemostatic valve and connected for access to the proximal end of the tubular extension. Several suitable designs are described herein. As noted in the discussion below, the fitting structures can be assembled for commercial elements or can be designed as a specific fitting particularly for the suction system and/or treatment systems described herein.

Figure 24:
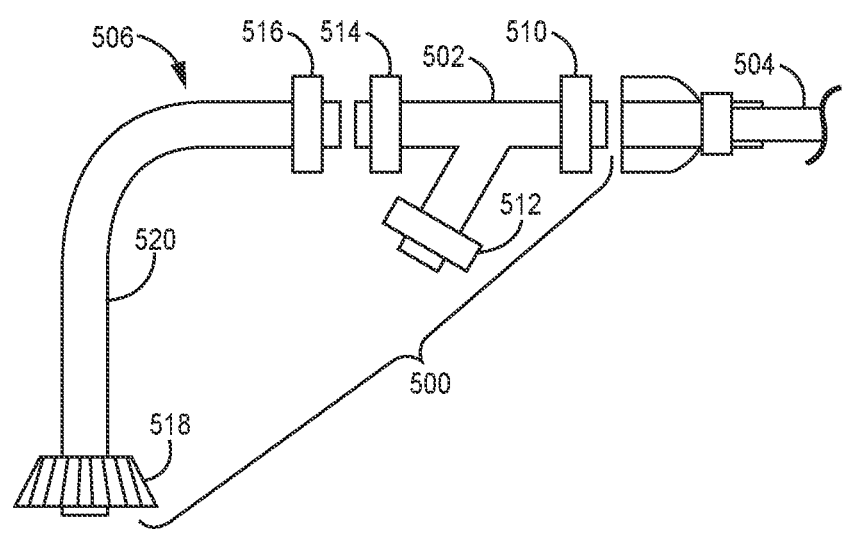
FIG. 24 is a fragmentary side view of proximal fittings shown with two separated components adjacent a guide catheter in which the two components are a Y-branch manifold and an extended hemostatic fitting.
Figure 25:
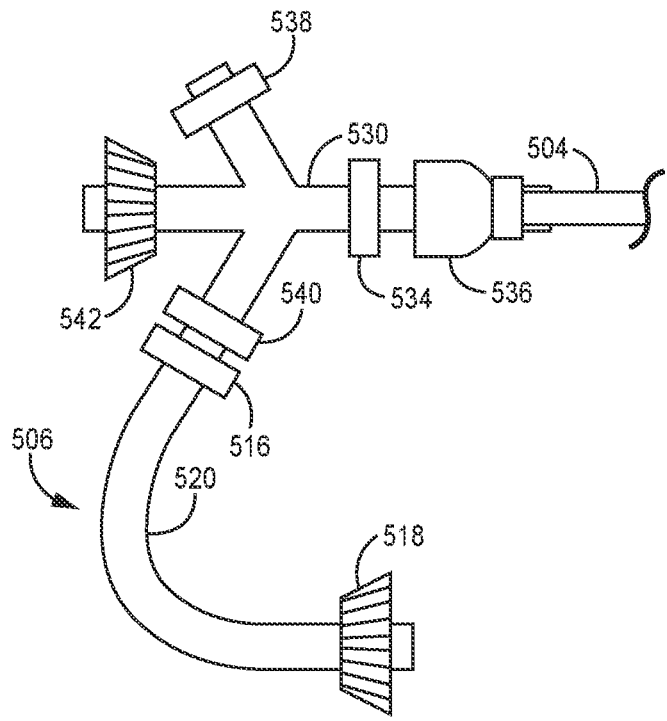
FIG. 25 is a fragmentary side view of an alternative embodiment of proximal fittings attached to a guide catheter with a three branch manifold extending from the guide catheter and an extended hemostatic fitting attached to one branch.
Figure 26:
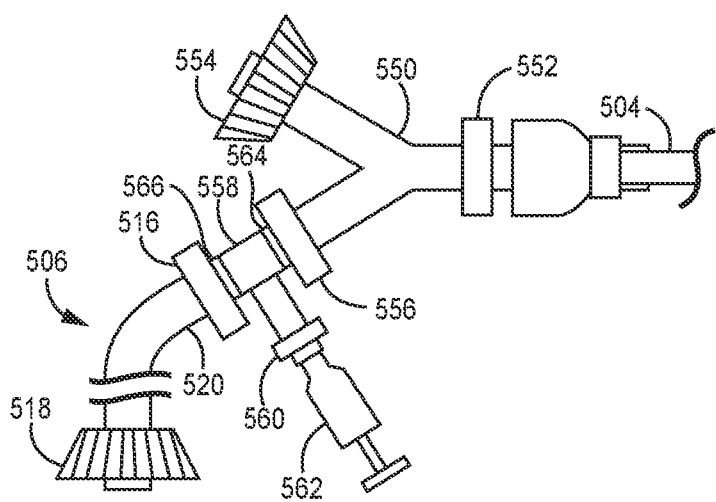
FIG. 26 is a fragmentary side view of a further alternative embodiment of proximal fittings extending from a guide catheter in which the fittings comprise a Y-branch manifold, a T-branch manifold connected to one branch of the Y and an extended hemostatic fitting extending from the straight branch of the T-branch and a negative pressure device attached along the T-branched conduit.

Three representative embodiments for proximal fittings are presented in FIGS. 24-26 in which the devices provide for holding a tubular extension of the suction extension within the manifold sealed behind a hemostatic valve or valves. As shown in FIGS. 24-26, the proximal fittings are assembled from a plurality of fitting components. But if desired, one or more of the components can be manufactured as a unitary structure with the corresponding elimination of one or more sets of connectors, and particular configurations can involve various tradeoffs, such as convenience of use, cost, packaging, standards in the art, flexibility of design during use, or the like. As shown in FIG. 24, the components are shown spaced apart, while for contrast, the multiple components are shown connected in FIGS. 25 and 26. Of course, for specific applications, additional components of the overall manifold can be assembled into the ultimate proximal fitting structure. For example, embodiments are shown below providing for attachment of a pressure sensor.

Referring to FIG. 24, fittings 500 comprises Y-branch manifold 502 suitable for connection with guide catheter 504, and extended hemostatic fitting 506. Guide catheter 504 can be any of the embodiments of guide catheters described above. Y-branch manifold 502 provides for multiple connectors with fluid communication with guide catheter 504. As shown in FIG. 24, Y-branch manifold 502 comprises three connectors 510, 512, 514, which can be Tuohy-Borst connectors, Luer connectors or other suitable connector. Connector 510 can be selected for connection with guide catheter 504. Connector 512 can be connected to a negative pressure source, such as a pump, or to further branched manifolds to provide for various connections such as for an infusion fluid source, generally with at least one connection to a negative pressure device. Connector 514 is configured to connect with extended hemostatic fitting 506. Extended hemostatic fitting 506 comprises connector 516 for a mated connection with Y-branch manifold 502, hemostatic valve 518 and tubular portion 520 between connector 516 and hemostatic valve fitting 518. Tubular portion 520 can have in some embodiments a suitable length for removing a tubular extension of a suction extension out from guide catheter 504 without passing any portion of the tubular extension or connecting section through the hemostatic valve, although a proximal control structure generally passes through the hemostatic valve, which is the possible configuration through the procedure.

The length of tubular portion 520 can be selected according to the length of the tubular extension as well as potentially if desired a relevant length of Y-branch manifold 502, which collectively can be referred to as a tubular section for placement of the tubular extension with the connecting section in hemostatic isolation outside of the guide catheter. It may or may not be desirable to withdraw the tubular extension fully into tubular portion 520 such that the remaining portions of the manifold are open. For the range of alternative embodiments considered for the proximal fittings of FIG. 24, the dimensions of the tubular section can be appropriately identified in the particular structure. In general, tubular portion 520 of extended hemostatic fitting 506 can have a length from about 8 cm to about 55 cm, in further embodiments from about 9 cm to about 50 cm, and in other embodiments from about 10 cm to about 45 cm. A person of ordinary skill in the art will recognize that additional ranges of lengths within the explicit ranges above are contemplated and are within the present disclosure.

In alternative or additional embodiments, extended hemostatic fitting 506 can comprise a tubular element with two connectors on either end and a separate hemostatic valve with a Luer or other connector on the opposite end that connect to each other to effectively form an equivalent structure to that shown in FIG. 24. Similarly, one or more additional fitting components can be connected using suitable connectors between extended hemostatic fitting 506 and Y-branch manifold 502, such as additional branched elements, and similarly additional fitting components can be connected at connector 512 to provide additional features to the fittings, such as connection of a pressure sensor or other structures. Thus, while providing the ability to withdraw a tubular extension within the closed fittings, the proximal fittings can be adapted with suitable structure to provide desired functionality. While this discussion has focused on the assembly of multiple fitting components to provide an overall fitting structure, one or more of these components can be formed as integral parts of a corresponding unitary structure, such as the integration of Y-branch manifold 502 and extended hemostatic fitting 506 into a unitary structure through the replacement of connectors 514 and 516 with a unitary section of tubing, and similar integration can be performed for adding additional structure. The unitary structure incorporating the features of Y-branch manifold 502 and extended hemostatic fitting 506 comprises a branched manifold with an extended hemostatic valve portion, which can be a suitable alternative to the structure in FIG. 24. Thus, various combinations of connecting elements, redesigning unitary components, and the like can be implemented to form a desired proximal fittings design.

Referring to an alternative configuration of a proximal fitting structure in FIG. 25, a three-branch manifold 530 is connected to guide catheter 504 and extended hemostatic fitting 520 is connected to a connector of one branch of three-branch manifold 530. Three-branch manifold 530 comprises first connector 534 connected to a proximal connector 536 of guide catheter 504, first branch connector 538, second branch connector 540 and hemostatic valve 542. Second branch connector 540 is connected to the extended hemostatic fitting 506, which is described in detail in the context of FIG. 24. First branch connector 536 can be connected to a negative pressure source directly or through a further branched manifold. Hemostatic valve 542 can be used for the introduction of supplemental treatment structures or other desirable devices. Again, the structure shown in FIG. 25 can be further divided into additional components if desired. For example, the three branch manifold can be effectively formed using two sequential Y-branch connectors. Again, additional fitting components can be connected onto the proximal fitting structure in FIG. 25 to provide additional features as described above in the context of FIG. 24. Also similarly, one or more separate components of the proximal fittings can be constructed as a unitary structure. Thus, component accretion and/or combination/joining processes can be combined for designing of a desired proximal fittings configuration.

Referring to FIG. 26, a further embodiment of proximal fittings is shown with a symmetric Y-branch structure. As shown in FIG. 26, symmetric Y-branch manifold 550 comprises first connector 552 connected to guide catheter 504, branched hemostatic valve 554 and branched connector 556. Branched connector 556 is connected with T-branch fitting 558. T-branch fitting 558 has a T-connector 560 that is shown connected with negative pressure device 562, such as a syringe or a pump. T-branch connector 556 is further connected with extended hemostatic fitting 506, which is described in detail in the context of FIG. 24 including but not limited to the dimensions of the element. T-branch connector 556 comprises connectors 564, 566 for respective connection with mated connectors 556, 516. The structure shown in FIG. 26 can be formed with multiple components used to form the structure, such as a separate component with hemostatic valve 554 connected with a suitable connector to a mated connector on symmetric Y-branch manifold 550, which is correspondingly modified. Again, additional fitting components can be connected onto the proximal fitting structure in FIG. 26 to provide additional features as described above in the context of FIG. 24. Also similarly, one or more separate components of the proximal fittings can be constructed as a unitary structure. Thus, component accretion and/or combination/joining processes can be combined for designing of a desired proximal fittings configuration.

The fittings can be formed from suitable materials for sterile assembly, which can involve in some embodiments subjecting the components to radiation. The components can be formed in either rigid and/or flexible materials such as polymers provided herein, and the connectors can be formed from suitable combination of materials for the formation of seals, such as elastomers. Rigid components can be formed, for example, from polycarbonate or other suitable polymer. The tubular portion 520 of extended hemostatic fitting 506 can be formed from a more flexible polymer, such as one or more of the polymers described above for the catheter body, for example, polyether-amide block co-polymer (PE-BAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, combinations thereof, or other suitable biocompatible polymers. As noted above, the various fitting structures can be assembled from additional components, added onto or subdividing the various components of the embodiments, and/or the components can be formed as integral structures correspondingly molded. Thus, particular designs can be assembled from existing commercially available components or all or a portion of the fittings can be produced specifically for these applications.

The proximal fittings can also be equipped with a pressure sensor to help guide the procedure. If a pump is used to supply negative pressure, the pressure set on the pump establishes a differential pressure limit. If fluid freely flows to the pump, the differential pressure in the conduits leading to the pump can be relatively low. If flow is effectively completely blocked, the gauge pressure in the line can be approximately the pump pressure, which is negative indicating suction. Intermediate pressure levels may be indicative of restrictions of flow due to normal catheter or suction extension configurations that can cause some flow resistance, or of less severe blockages to the flow from various potential sources. In any case, as explained further below, having a measure of the line pressure in the proximal fittings can provide valuable information to assist in the procedure.

Figure 27:
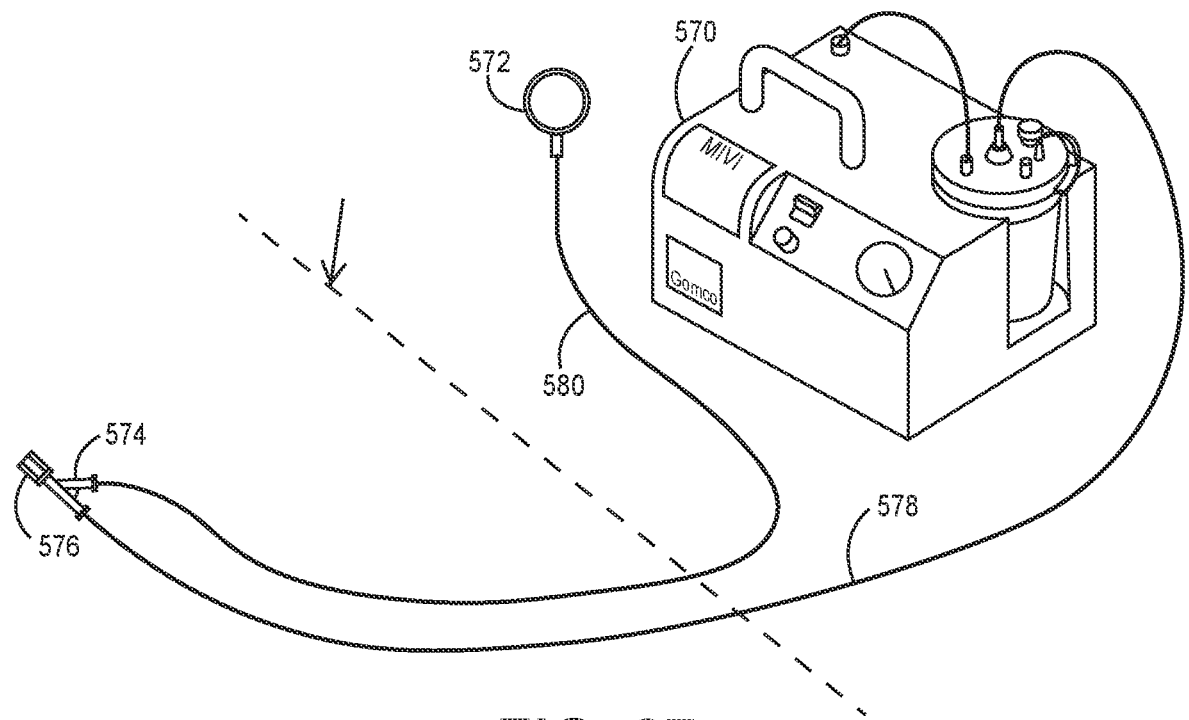
FIG. 27 is a perspective view of a Y-branch manifold adapted for connection with a pmp and to a pressure sensor.
Figure 28:
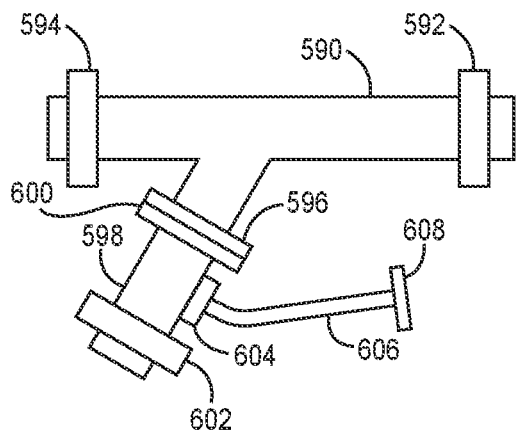
FIG. 28 is a side view of a Y-branch manifold attached to a tubular fitting adapted with a pressure sensor having an electronic connector.
Figure 29:
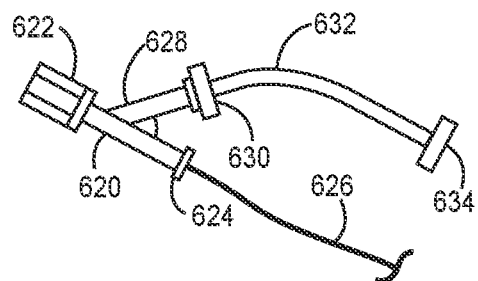
FIG. 29 is a side view of a Y-branch manifold with a terminal pressure sensor along one branch and with an electrical connector for connection with the pressure sensor.

There are various possible configurations for a pressure sensor in association with the proximal fittings, and three representative embodiments are shown in FIGS. 27-29. Referring to FIG. 27, a pump 570 and pressure gauge 572 are connected to a Y-manifold 574 that comprises a connector 576 that can be attached to manifold connectors in the fittings connected to the guide catheter, such as shown in FIGS. 5 and 24-26. Pump 570 and pressure gauge 572 can be connected, respectively, using tubing 578, 580 to Y-manifold 574. The connections of tubing 578, 580 to Y-manifold 574 can be achieved at suitable connectors or they can be formed integral to the component. In this embodiment, pump 570 and optionally pressure gauge 572 may not be sterile, but no flow is intended to go to the patient from these devices. If the non-sterile components are appropriately isolated from the patient's fluids, the configuration can be acceptable even though the devices are not sterile. A selected length, for example 6 feet, dividing line to provide for appropriate sterile isolation is schematically denoted in FIG. 27 with a dashed line noted with an arrow. Commercial aspiration pumps for medical applications, in which some specific pumps are noted above, can operate at gauge pressures from about −1 to about −26 inches of mercury (−25 mmHg to −660 mmHg). High pressure tubing is also available for medical applications, e.g., from MIVI Neuroscience, Inc. or Penumbra, Inc.

A further embodiment of a fitting adapted with a pressure sensor is shown in FIG. 28. The fitting component in FIG. 28 comprises a Y-branch connector 590 with a distal connector 592, a proximal connector 594 and branch connector 596, and a pressure sensor component 598 with a first connector 600 shown connected with branch connector 590 and second connector 602. Pressure sensor component 598 further comprises pressure sensor 604 installed on the side wall of pressure sensor component 598. Electrical wires 606 extend from pressure sensor 604 and terminate at electrical connector 608, which can be a multi-pin clip or other suitable connector configuration. Electrical connector 608 can be suitable for connection to a suitable monitor or display. Commercial pressure sensor components for use as pressure sensor component 598 are commercially available, for example, from PendoTECH, Princeton, NJ, USA. These components can be purchased sterile or they can be sterilized before use using conventional methods, such as using gamma irradiation. A pump or other negative pressure device can be connected to second connector 602 or other appropriate portion of the finally assembled proximal fittings.

Another embodiment of a fitting component adapted with a pressure sensor is shown in FIG. 29. In this embodiment, Y-manifold 620 comprises a connector 622 for connection to other components of the proximal fittings and a connector 624 connected to tubing 626 for connection to a pump or the like. Y-manifold 620 further comprises a branch 628 adapted with a pressure sensor 630 at the end of the conduit. Pressure sensor 630 can be adapted on a connector cap or it can be bonded in a sealed configuration with branch 628, or otherwise adapted appropriately with a sealed attachment. Pressure sensor 630 is operably attached to electrical cable 632 which terminates at an electrical connector, such as a multi-pin clip. Pressure sensor dies or assemblies suitable for medical use are commercially available, such as from Merit Medical Systems, Inc. (Merit Sensors), which can be adapted for such connections.

Procedures Making Use of Treatment Systems

As indicated above, the medical systems comprising a suction catheter system described herein can be used with the suction catheter system as stand-alone treatment device, perhaps with a guidewire and/or other delivery support devices, or used with supplemental medical treatment devices for treatment of ischemic vessel blockage. In particular, in some embodiments, the suction system is used with an embolic protection device, and in additional embodiments, some form of clot engagement device, stent, balloon, atherectomy device or the like may also be used. In any case, a guidewire is generally used to provide access to the treatment site. The guide catheter portion of the suction catheter system may or may not be positioned prior to the introduction of the suction extension. The structures of the particular components are described in detail above, and are not repeated so that this section can focus on the use of the devices.

Figure 30:
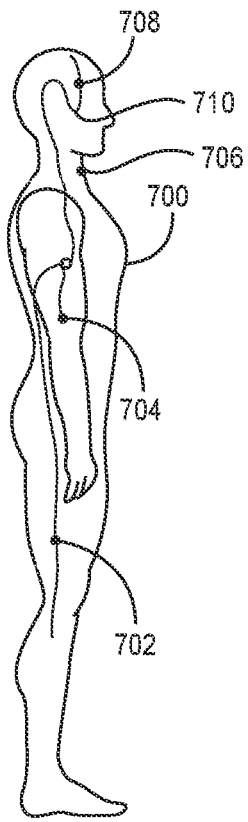
FIG. 30 is a schematic depiction of a human patient with alternative access approaches for directing catheters into the blood vessels of the brain.
Figure 31:
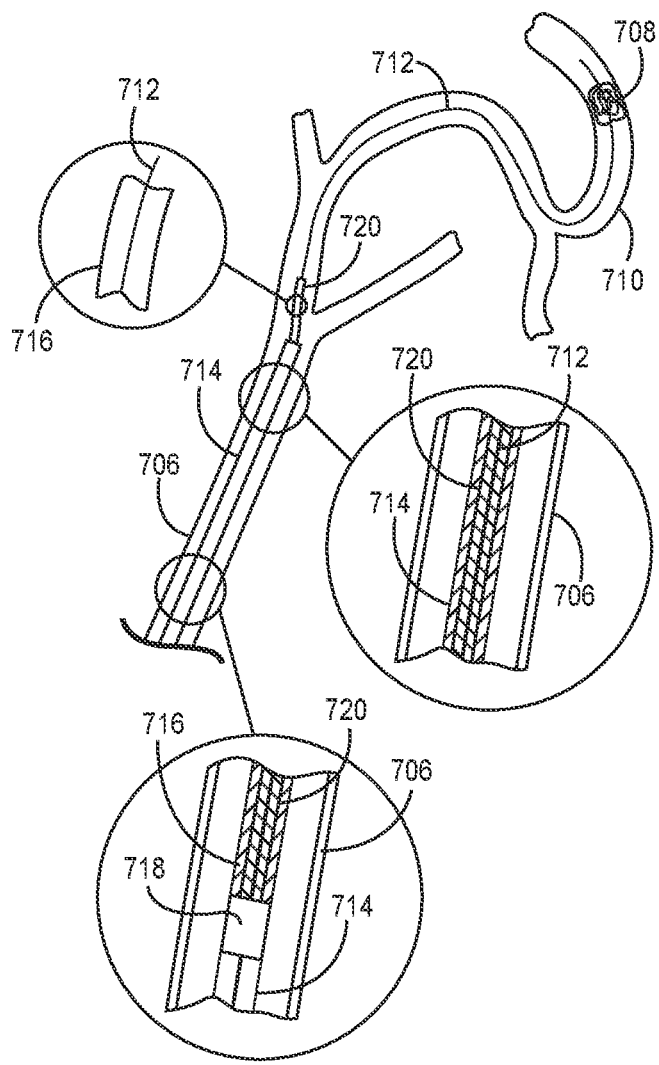
FIG. 31 is a view within a branched blood vessel section showing the delivery of medical devices along a guidewire from a guide catheter to a clot. Inserts show expanded views of two internal sections of the guide catheter.
Figure 32:
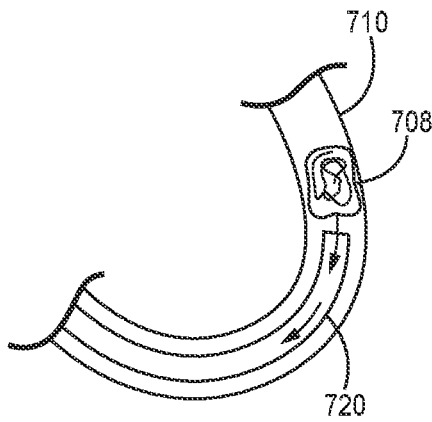
FIG. 32 is a schematic view in a section of blood vessel of a suction system being used to remove a clot.

For the treatment of an acute ischemic stroke condition, referring to FIG. 30, a patient 700 is shown with three alternative access points into the vasculature, femoral artery 702, artery in the arm 704 or carotid artery in the neck 706. Regardless of the access point, the catheter and associated devices are guided to the left or right carotid artery to reach a clot 508 in a cerebral artery 710 of the brain. Referring to the schematic view in FIG. 31, clot 708 is shown in cerebral artery 710 with a guidewire 712 positioned with its distal tip past the clot. Guide catheter 714 is positioned over the guidewire within the carotid artery 706. Suction extension 716 with connecting section 718 within guide catheter 714 and tubular extension 720 extending from guide catheter 714 over guidewire 712. Referring to FIG. 32, tubular extension 720 can be advanced over the guidewire to a position near clot 708. Suction can be applied as shown with the flow arrows in the figure. Guidewire 712 may or may not be removed before suction is applied. Suction catheters have successfully removed clots responsible for ischemic stroke without further medical devices in the intervention. However, for more difficult clots, additional medical treatment devices can be used as described in detail below.

Using the embodiments of proximal fittings, such as shown in FIGS. 27-29, adapted with pressure sensing capability, the initiation of suction as described in the context of FIG. 32 can be checked with respect to its efficacy. If appropriate flow is established since negative pressure is applied to the catheter system, the pressure in the proximal fittings can be in a suitable range. The precise ranges of expected pressures generally are dependent on the specific design of the suction extension, and the acceptable pressure range can be adjusted accordingly. In any case, the pressure can be confirmed in real time during the procedure for comparison with specifications adapted for the specific suction catheter components. If the pressure at the time immediately following the initiation of suction is closer to the negative pressure of the pump than expected based on the set acceptable range, the physician can withdraw the suction extension at least part way from the delivered configuration with or without stopping suction. A partial withdrawal can be used to try to unkink the suction extension without complete removal. As described further below, if proximal fittings are used that allow removal of the tubular extension for the patient without passing through a hemostatic valve, the tubular extension can be visually checked without exposing the tubular extension to the ambient atmosphere. After verifying that the tubular extension is ready for use or after replacing the suction extension, the suction extension can be redelivered.

Figure 33:
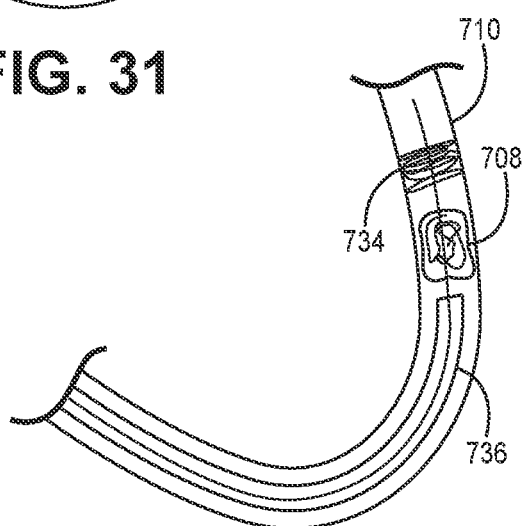
FIG. 33 is a schematic view in a section of blood vessel with a suction system positioned upstream from a clot and a fiber based filter deployed downstream from the clot.
Figure 34:
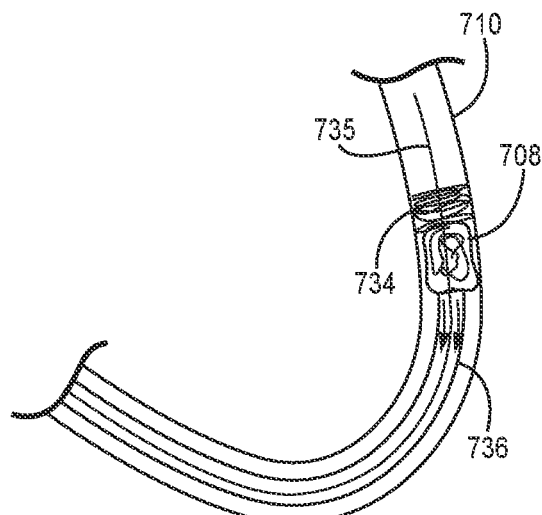
FIG. 34 is a schematic view of the section of blood vessel of FIG. 33 with the fiber based filter being drawn toward the suction tip to draw the clot to the tip for facilitating removal of the clot.

Referring to FIGS. 33 and 34, the use of a fiber-based filter device is shown in use along with the suction catheter system. As shown in FIG. 33, clot 708 is shown in cerebral artery 710 with a deployed fiber-based filter 734 supported on a guidewire 736 positioned with the filter deployed past the clot. Fiber-based filter 734 can have fiber elements extending essentially to the wall of the vessel, cerebral artery 710. Tubular extension 736 can be positioned with its distal tip just proximal to the clot, and the remaining portions of the suction catheter system are not shown in this view. Referring to FIG. 34, fiber-based filter 734 can be pulled toward tubular extension 736 with suction being applied to facilitate removal of clot 730. Clot 708 can be broken up and removed by suction, and/or all or a portion of clot 708 can be pulled into tubular extension 736 optionally along with all or part of the fiber-based filter, and/or all or a portion of clot 708 can be held to the opening of tubular extension 736 with the fiber-based filter holding the clot. In any case, once the clot is appropriately stabilized, the devices and any clot still within the vessel or catheter can be removed from the patient. The removal of the devices is described further below.

Figure 35:
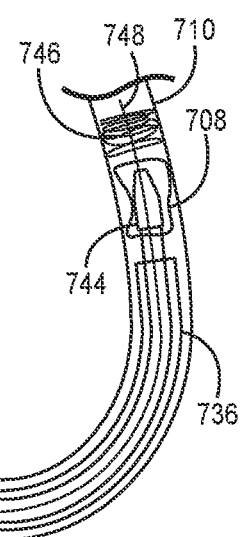
FIG. 35 is a schematic view of a section of blood vessel with a suction system positioned upstream from a clot, a fiber based filter deployed downstream from the clot and another medical device positioned at the clot.
Figure 36:
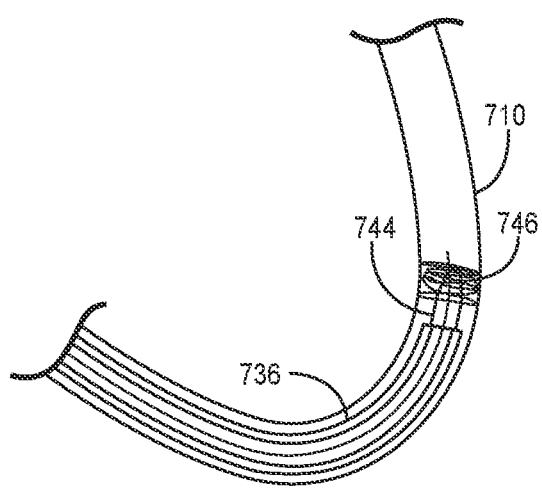
FIG. 36 is a schematic view of the section of blood vessel of FIG. 35 with the various medical devices being used in concert for the removal of the clot.

The further use of an additional medical device to facilitate clot removal is shown in FIGS. 35 and 36. As shown in FIG. 35, clot 708 is shown in cerebral artery 710 with a medical treatment device 754 positioned at the clot and deployed fiber-based filter 756 supported on a guidewire 758 positioned with the filter deployed past the clot. Suitable medical treatment devices for clot engagement are described above. The selected medical treatment device is deployed generally with protection from the deployed fiber-based filter and optionally with suction. Once the clot is engaged with the medical treatment device, the recovery of the remaining portions of the clot and the medical treatment devices can be removed as shown in FIG. 36, similarly to the process shown in FIG. 35. In particular, the medical treatment device can be removed, although portions such as a stent may be left behind, and the removal can precede or be done in conjunction with removal of a filter and/or remaining fragments of clot. All or a portion of clot 708, if not already broken up and removed with suction can be pulled into tubular extension 736 optionally along with all or part of the fiber-based filter, and/or all or a portion of clot 708 can be held to the distal opening of tubular extension 736 with the fiber-based filter holding the clot. Again, once the clot is appropriately stabilized, the devices and any clot still within the vessel or catheter can be removed from the patient. The use of a plurality of additional medical treatment devices can be performed through extension of the procedure outlined above to repeat steps involving the additional medical device.

Also, for the embodiments in FIGS. 33-36, a pressure sensor connected to the proximal fittings can be used to guide the procedures. If the pressure in the proximal fittings increases to a pressure outside of a target range when negative pressure is initiated, appropriate remedial attention can be applied to remove a kink or replace the suction extension or other appropriate attention. Also, after suction is applied and the clot seems to have been addressed, the pressure in the proximal fittings can be checked to evaluate the status of the clot and the catheter, such as whether or not the clot is trapped at the distal end of the suction extension. Appropriate care can be taken based on the pressure in the proximal fittings.

Figure 37:
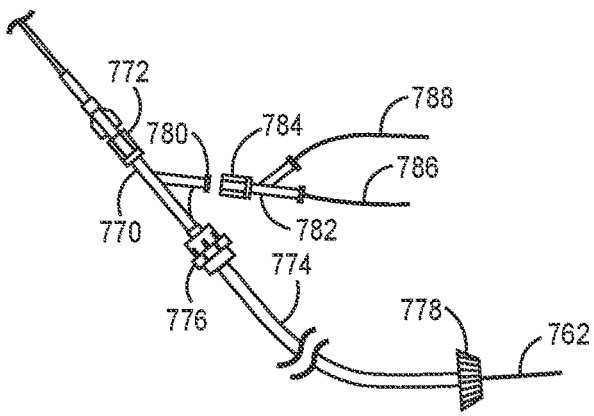
FIG. 37 is a fragmentary view of a treatment system extending from a position in the neuro-vasculature to the proximal fittings shown following application of suction and optionally other procedural steps to remove a clot, with an insert in the figure showing a sectional view of a tubular extension within a guide catheter.

FIG. 37 depicts the suction treatment system following treatment of a clot in cerebral artery 750. Tubular extension 752 is positioned with its distal tip in cerebral artery 750 and thrombus 754 may or may not be present at the opening. Guide catheter 756 is located with its distal end in carotid artery 758. A section of the interior of guide catheter 756 is shown in a balloon insert of FIG. 37. Connecting section 760 of suction extension 752 is within guide catheter 756 with control wire 762 extending in a proximal direction. The patient's leg 764 is shown with an introducer sheath 766 extending from the leg with a hemostatic valve 768. Guide catheter 756 extends out from hemostatic valve 768. Y-branch manifold 770 is connected to the distal end of guide catheter 756 at connector 772. Extended hemostatic fitting 774 is connected with Y-branch manifold 770 at connector 776, and terminates with a hemostatic valve 778. Control wire 762 extends from hemostatic valve 778. Y-branch manifold 770 has a connector 780 that can be connected to a further Y-branch manifold 782 with connector 784 for connection to connector 780. Y-branch manifold can be connected to a negative pressure line 786 that can be connected to a pump or other negative pressure device, and to a pressure sensor line 788 that can be connected to an appropriate pressure sensor such as those of FIGS. 27-29.

Figure 38:
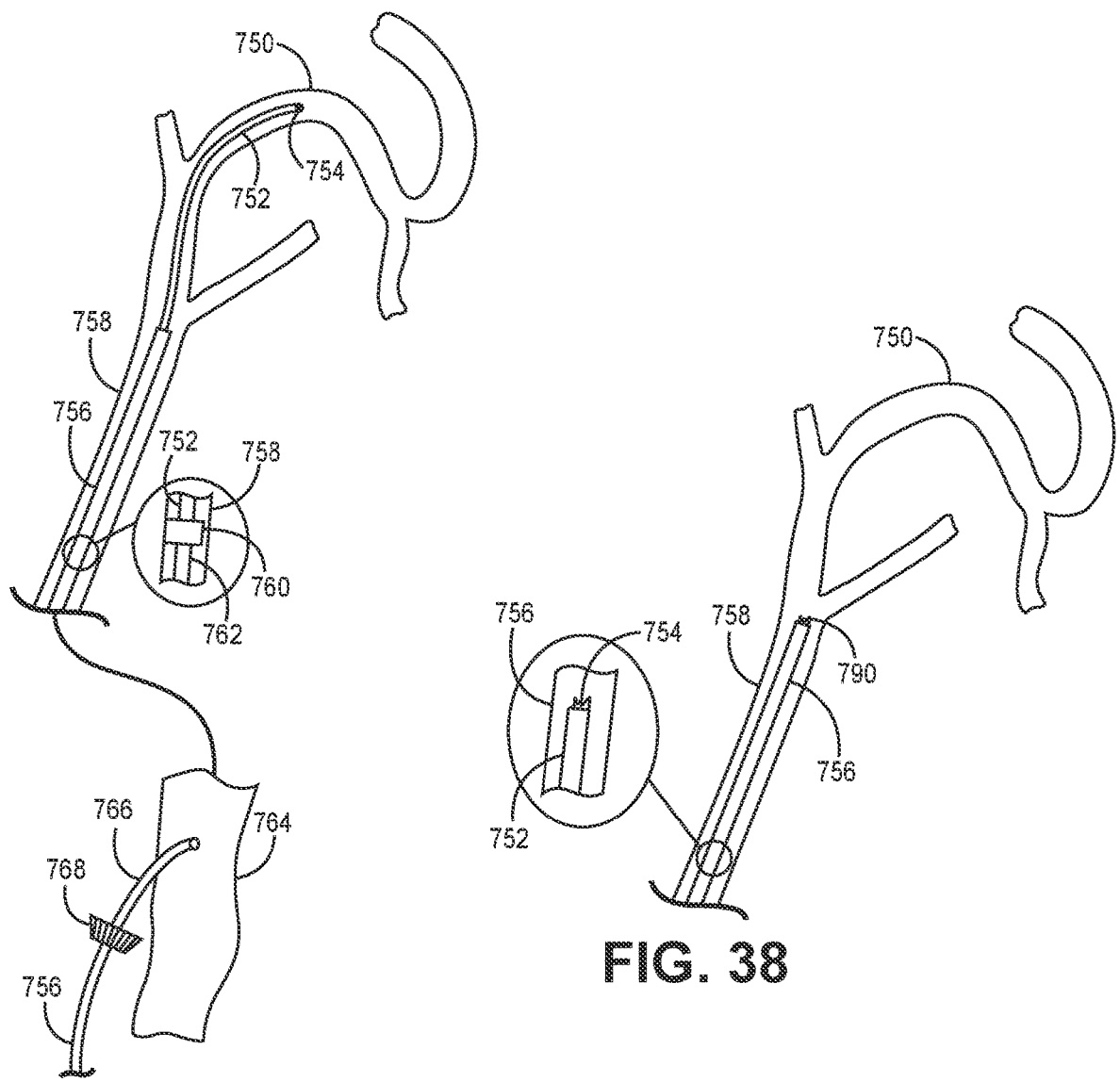
FIG. 38 is a fragmentary view of the distal portion of the treatment system of FIG. 37 in which the tubular extension is withdrawn into the guide catheter, with an insert of the figure showing sectional view of the distal end of the tubular extension within the guide catheter.

At the stage of the procedure shown in FIG. 37, procedural steps can be initiated for gradual removal of the devices from the patient. It can be advantageous to maintain the guide catheter in position while removing the other components and verifying the success of the procedure. Generally, it is desired to keep the guide catheter in place until the procedure is to be completely ended since the guide catheter placement involves significant effort. Pressure readings at the proximal fittings can provide useful information regarding the status of potential blockages of flow into suction extension 752. Referring to FIG. 38, guide catheter 756 is still in place in carotid artery 758 and cerebral artery 750 is clear of devices and clot. Referring to the balloon figure insert associated with FIG. 38, a further enlarged sectional view shows the distal end of suction extension 752 within the interior of guide catheter 756. Thrombus may or may not be associated with the distal end of guide catheter 756 (thrombus 790), which can be deposited there when suction extension 752 is withdrawn into guide catheter 756, and/or at the distal end of suction extension 752 (thrombus 754). Again, a pressure reading in the proximal fittings can provide useful information on potential thrombus blocking flow through the catheter system to the negative pressure device, such as a pump.

Figure 39:
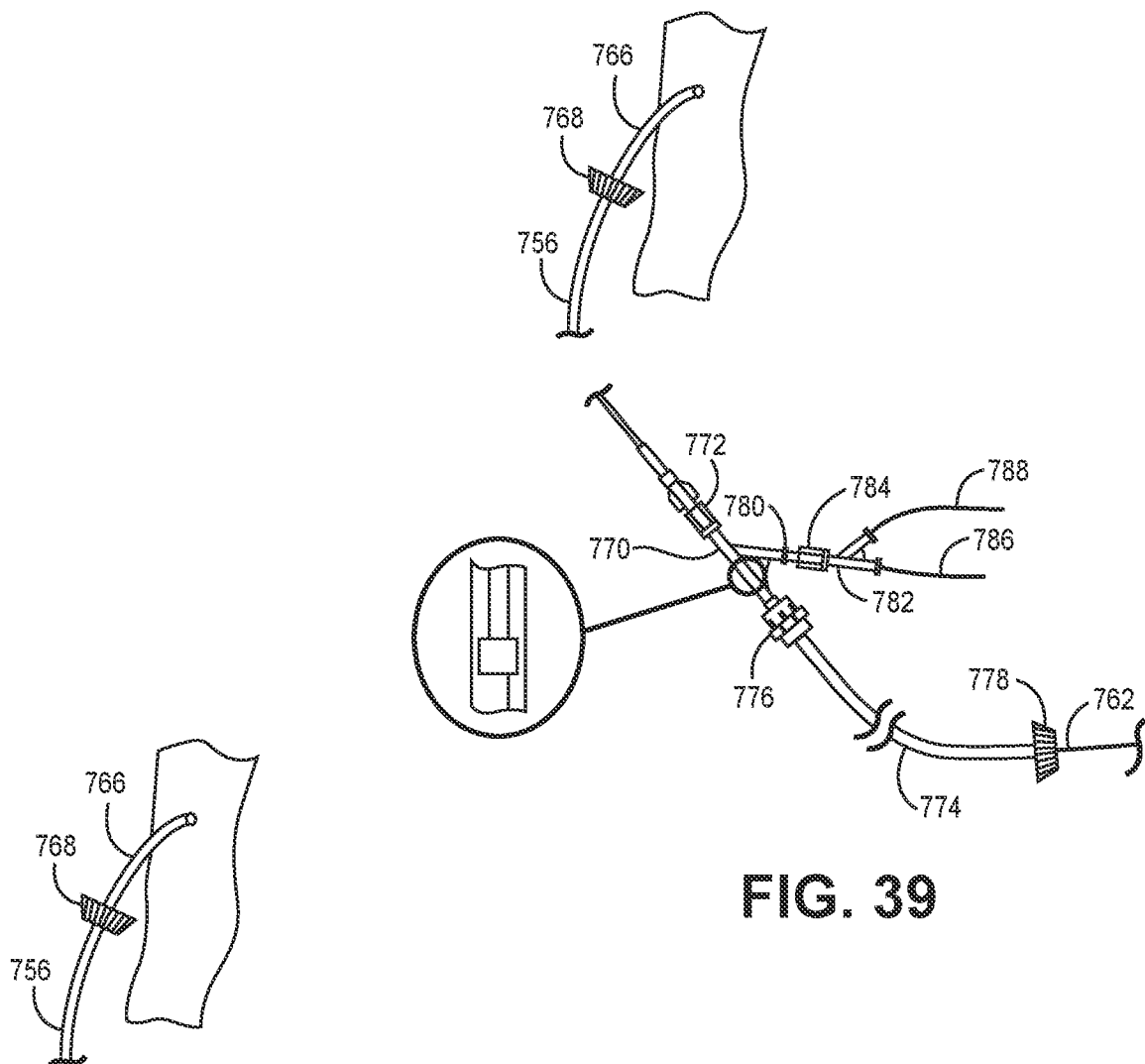
FIG. 39 is a fragmentary view of the proximal end of the treatment system of FIG. 37 in which the tubular extension is withdrawn sufficiently such that a connection section of the suction extension is within proximal fittings external to the guide catheter as shown in the sectional view of the figure insert.

Referring to FIG. 39, upon further withdrawal of suction extension 752 from the patient, a balloon figure insert shows a further enlarged section view with connecting section 760 of suction extension 752 within T-branch manifold 770. With this configuration, a continuation of application of negative pressure would draw fluid from guide catheter 756 rather than through suction extension 752. Whether or not suction extension 752 is plugged, this configuration can provide addition possibility of removal of thrombus 790 at the end of guide catheter 756, and the suction can further stabilize thrombus 790, if any, for further portions of the procedure. At this stage of the procedure, the pressure in the proximal fittings can provide information on the flow of liquid into guide catheter 756.

Figure 40:
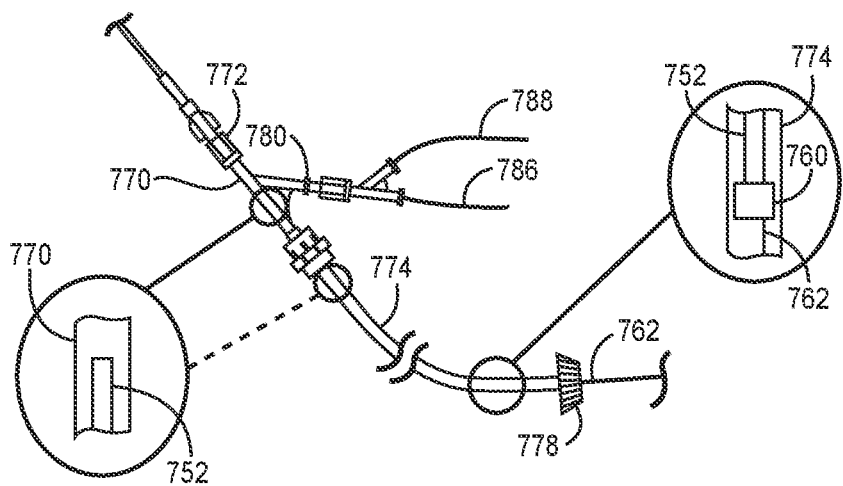
FIG. 40 is a fragmentary view of the proximal end of the treatment system of FIG. 37 in which the tubular extension is withdrawn from the guide catheter but remains enclosed in the proximal fittings with sealed hemostatic valves, with a left figure insert showing a sectional view of the distal end of tubular extension within a Y-branch manifold (and an alternative placement of the distal extension within extended hemostatic fitting noted with a dashed line) and a right figure insert showing the connection section of the suction extension within an extended hemostatic fitting with a control wire extending through a hemostatic valve.

The complete removal of suction extension 752 from guide catheter 756 is shown in FIG. 40. A distal balloon figure insert in FIG. 40 shows a further expanded section view with the distal end of suction extension 752 within T-branch manifold 770, although the distal end of suction extension 752 can be withdrawn fully into extended hemostatic fitting 774 as noted by the dashed line connected to the balloon figure insert. A proximal balloon figure insert in FIG. 40 shown a further expanded sectional view with connection section 760 within extended hemostatic fitting 774 in a position distal to hemostatic valve 778. Again, pressure within proximal fittings can be useful to provide information during this part of the procedure.

While guide catheter 756 can be removed from the patient following treatment of the clot, it can be desirable to at least partially remove suction extension 752 relative to its deployed location with the guide catheter in position to reduce the risk of embolization of thrombus that may be trapped in association with the aspiration system components but not yet fully removed from the patient. FIGS. 38-40 depict three stages of suction extension removal at which time it can be selected to remove guide catheter 756 from the patient, generally through hemostatic valve 768 of introducer 766. With the distal end of suction extension 752 within guide catheter 756, as shown in FIG. 38, any thrombus associated with suction extension 752 is within guide catheter 756 so that it is less likely to involve embolization. Referring to FIG. 39, as noted above, connection section 760 within Y-branch manifold 770, suction is applied directly to guide catheter 756 lumen regardless of whether or not suction extension 752 is clogged, and this direct application of suction to guide catheter 756 provides an added degree of safety with respect to reducing chances of embolization. Furthermore, complete removal of suction extension 752 from guide catheter 756, as shown in FIG. 40, provides additional safety against embolization of thrombus associated with suction extension 752. As shown in FIG. 40, suction extension 752 remains in isolation behind a hemostatic valve 778, and this configuration provides for desirable control of pressures within guide catheter 756 that further reduces risk of embolization as well as contamination.

The suction catheter system is generally appropriately sterilized, such as with e-beam or gas sterilization. The suction catheter system components can be packaged together or separately in a sealed package, such as plastic packages known in the art. The package will be appropriately labeled, generally according to FDA or other regulatory agency regulations. The suction catheter system can be packaged with other components, such as a guidewire, filter device, and/or other medical device(s). The packaged system generally is sold with detailed instructions for use according to regulatory requirements.

Bench testing and calculations were performed to evaluate the general suction performance of the use of a suction extension interfaced with a guide catheter and for other commercial suction catheters. These results are described in the '938 application, and are incorporated herein by reference.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. To the extent that specific structures, compositions and/or processes are described herein with components, elements, ingredients or other partitions, it is to be understood that the disclosure herein covers the specific embodiments, embodiments comprising the specific components, elements, ingredients, other partitions or combinations thereof as well as embodiments consisting essentially of such specific components, ingredients or other partitions or combinations thereof that can include additional features that do not change the fundamental nature of the subject matter, as suggested in the discussion, unless otherwise specifically indicated.

What is claimed is:

1. A suction catheter system comprising:
a guide catheter comprising a tubular shaft with a central lumen, and having a proximal end and a distal opening;
a suction extension comprising a connecting section with a central lumen; a tubular extension comprising a tube that is connected with the connecting section and extends from the connecting section in a distal direction; and a control structure comprising an elongated structure extending from the connecting section in a proximal direction, wherein the connecting section is configured to slide within at least a portion of the central lumen of the guide catheter to change the relative position of the connecting section within the central lumen and provide for at least a portion of tubular extension to extend outward from the distal opening of the tubular shaft; and
proximal fittings comprising a primary branched manifold with a first branch having a hemostatic valve with the control structure extending through the hemostatic valve, with a second branch connected to a secondary branched manifold with a first branch connected to a negative pressure device, and with a second branch connected to a pressure sensor configured to measure the pressure in the second branch of the primary branched manifold, wherein the proximal fittings are connected to the proximal end of the guide catheter and wherein the pressure sensor is connected to a display that is configured to display a pressure value.

2. The suction catheter system of claim 1 wherein the pressure sensor comprises a pressure transducer associated with a wall of the second branch.

3. The suction catheter system of claim 1 wherein the second branch of the manifold comprises a connector attached to a pressure sensor.

4. The suction catheter system of claim 1 wherein a connector on the second branch of the manifold is connected to tubing that is connected with a pressure gauge.

5. The suction catheter system of claim 1 wherein the second branch of the manifold is connected to tubing connected to a pump that is rated to generate a negative pressure from about −1 to about −26 inches of mercury (−25 mmHg to −660 mmHg).

6. The suction catheter system of claim 5 wherein the pressure sensor is configured to provide information on the suction status.

7. The suction catheter system of claim 5 wherein the suction extension is configured to be withdrawn with the application of negative pressure into tubing such that the suction extension is withdrawn from the guide catheter with the suction extension remaining isolated behind the hemostatic valve.

8. The suction catheter system of claim 1 wherein a tubular segment provides a length between the hemostatic valve and the proximal end of the tubular shaft of the guide catheter that is at least as long as the length of the tube of the suction extension.

9. The suction catheter system of claim 1 wherein the connecting section has a non-circular cross section.

10. The suction catheter system of claim 1 wherein the length from the proximal end of the guide catheter to the hemostatic valve is from about 8 cm to about 55 cm.

11. The suction catheter system of claim 1 wherein the proximal fittings comprise a third branch connected to an infusion fluid source.

12. The suction catheter system of claim 11 wherein the infusion fluid comprises contrast dye.

13. The suction catheter system of claim 11 wherein the infusion fluid comprises a therapeutic agent.

14. The suction catheter of claim 1 wherein the primary branched manifold is connected to the guide catheter.

15. The suction catheter of claim 14 wherein the primary branched manifold is formed from a plurality of component attached to each other with connectors.

16. The suction catheter of claim 14 wherein the primary branched manifold is a unitary component.

17. The suction catheter of claim 1 wherein the negative pressure device comprises a pump connected to the second branch of the primary branched manifold by tubing.

18. A suction catheter system comprising:
a guide catheter comprising a tubular shaft with a central lumen, and having a proximal end and a distal opening;
a suction extension comprising a connecting section with a central lumen; a tubular extension comprising a tube that is connected with the connecting section and extends from the connecting section in a distal direction; and a control structure comprising an elongated structure extending from the connecting section in a proximal direction, wherein the connecting section is configured to slide within at least a portion of the central lumen of the guide catheter to change the relative position of the connecting section within the central lumen and provide for at least a portion of tubular extension to extend outward from the distal opening of the tubular shaft; and
proximal fittings comprising a branched manifold with a first branch having a hemostatic valve with the control structure extending through the hemostatic valve, with a second branch connected to a negative pressure device, and with a pressure sensor configured to measure the pressure in the second branch, wherein the proximal fittings are connected to the proximal end of the guide catheter and wherein the pressure sensor is connected to a display that is configured to display a pressure value,
wherein the connecting section has a non-circular cross section.

* * * * *